(12) United States Patent
Witt et al.

(10) Patent No.: US 12,397,039 B2
(45) Date of Patent: Aug. 26, 2025

(54) COMPOSITIONS AND METHODS FOR THE TREATMENT OF OCULAR NEOVASCULARIZATION

(71) Applicant: NOVALIQ GMBH, Heidelberg (DE)

(72) Inventors: Madlen Witt, Heidelberg (DE); Claus Cursiefen, Cologne (DE); Felix Bock, Cologne (DE)

(73) Assignee: NOVALIQ GMBH, Heidelberg (DE)

( * ) Notice: Subject to any disclaimer, the term of this patent is extended or adjusted under 35 U.S.C. 154(b) by 861 days.

(21) Appl. No.: 17/431,059

(22) PCT Filed: Feb. 11, 2020

(86) PCT No.: PCT/EP2020/053405
§ 371 (c)(1),
(2) Date: Aug. 13, 2021

(87) PCT Pub. No.: WO2020/165132
PCT Pub. Date: Aug. 20, 2020

(65) Prior Publication Data
US 2022/0143137 A1 May 12, 2022

(30) Foreign Application Priority Data

Feb. 13, 2019 (EP) .................................. 19156934
Apr. 29, 2019 (EP) .................................. 19171487

(51) Int. Cl.
*A61K 38/17* (2006.01)
*A61K 9/00* (2006.01)
(Continued)

(52) U.S. Cl.
CPC .......... *A61K 38/179* (2013.01); *A61K 9/0048* (2013.01); *A61K 9/10* (2013.01); *A61K 47/06* (2013.01); *A61P 27/02* (2018.01)

(58) Field of Classification Search
None
See application file for complete search history.

(56) References Cited

U.S. PATENT DOCUMENTS 2,616,927 A   11/1952  Kauck et al.
4,452,818 A    6/1984  Haidt
(Continued)

FOREIGN PATENT DOCUMENTS

CN   200977281 Y   11/2007
CN   202136470 U    2/2012
(Continued)

OTHER PUBLICATIONS

The Diabetic Retinopathy Clinical Research Network, New Engl. J. Med. 372:1193-1203 (2015) (Year: 2015).*
(Continued)

*Primary Examiner* — Karl J Puttlitz
(74) *Attorney, Agent, or Firm* — Hoxie & Associates LLC

(57) ABSTRACT

The present invention relates to a non-aqueous ophthalmic composition comprising particles of a protein powder preparation suspended in a liquid vehicle comprising a semifluorinated alkane, wherein the particles of the protein powder preparation comprise an anti-VEGF protein selected from aflibercept or a sequence having at least 90% sequence identity to SEQ ID NO: 1. The composition is particularly suitable for the treatment of ocular neovascularization.

14 Claims, 4 Drawing Sheets

Specification includes a Sequence Listing.

(51) Int. Cl.
  *A61K 9/10* (2006.01)
  *A61K 47/06* (2006.01)
  *A61P 27/02* (2006.01)

(56) References Cited

U.S. PATENT DOCUMENTS

| | | |
|---|---|---|
| 5,077,036 A | 12/1991 | Long, Jr. |
| 5,152,997 A | 10/1992 | Ebert et al. |
| 5,254,338 A | 10/1993 | Sakai et al. |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino |
| 5,851,544 A | 12/1998 | Penska et al. |
| 5,874,469 A | 2/1999 | Maniar et al. |
| 5,874,481 A | 2/1999 | Weers |
| 5,904,933 A | 5/1999 | Riess et al. |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,264,990 B1 | 7/2001 | Knepp et al. |
| 6,294,563 B1 | 9/2001 | Garst |
| 6,335,335 B2 | 1/2002 | Higashiyama |
| 6,372,243 B2 | 4/2002 | Kobuch et al. |
| 6,391,879 B1 | 5/2002 | Reeves |
| 6,399,087 B1 | 6/2002 | Zhang et al. |
| 6,458,376 B1 | 10/2002 | Meadows |
| 6,486,212 B2 | 11/2002 | Meinert |
| 6,489,367 B1 | 12/2002 | Meinert |
| 6,528,086 B2 | 3/2003 | Zhang |
| 6,730,328 B2 | 5/2004 | Maskiewicz |
| 7,001,607 B1 | 2/2006 | Menz |
| 7,026,359 B1 | 4/2006 | Gross |
| 7,087,237 B2 | 8/2006 | Peyman |
| 7,258,869 B1 | 8/2007 | Berry |
| 7,608,261 B2 | 10/2009 | Furfine et al. |
| 7,687,455 B2 | 3/2010 | Bonnet et al. |
| 7,740,875 B2 | 6/2010 | Dechow |
| 8,029,977 B2 | 10/2011 | Meinert et al. |
| 8,222,292 B2 | 7/2012 | Goskonda et al. |
| 8,470,873 B2 | 6/2013 | Chen |
| 8,614,178 B2 | 12/2013 | Theisinger et al. |
| 8,759,281 B2 | 6/2014 | Bonnet et al. |
| 8,796,340 B2 | 8/2014 | Theisinger et al. |
| 8,865,131 B2 | 10/2014 | Hagedorn et al. |
| 8,916,157 B2 | 12/2014 | Krause et al. |
| 8,916,158 B2 | 12/2014 | Krause et al. |
| 8,986,738 B2 | 3/2015 | Meinert |
| 9,000,048 B2 | 4/2015 | Mecozzi et al. |
| 9,072,668 B2 | 7/2015 | Dai et al. |
| 9,241,900 B2 | 1/2016 | Wilson |
| 9,308,262 B2 | 4/2016 | Wilson |
| 9,446,026 B2 | 9/2016 | Bingaman et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 9,968,678 B2 | 5/2018 | Theisinger et al. |
| 9,982,032 B2 | 5/2018 | Park et al. |
| 10,045,996 B2 | 8/2018 | Theisinger et al. |
| 10,058,615 B2 | 8/2018 | Günther et al. |
| 10,064,944 B2 | 9/2018 | Wilson |
| 10,130,707 B2 | 11/2018 | Günther et al. |
| 10,273,298 B2 | 4/2019 | Günther et al. |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 | 10/2020 | Löscher et al. |
| 10,813,999 B2 | 10/2020 | Günther et al. |
| 11,135,266 B2 | 10/2021 | Kerwin et al. |
| 11,154,513 B2 | 10/2021 | Scherer et al. |
| 11,160,865 B2 | 11/2021 | Theisinger et al. |
| 11,273,174 B2 | 3/2022 | Löscher et al. |
| 11,278,503 B2 | 3/2022 | Günther et al. |
| 11,324,757 B2 | 5/2022 | Theisinger et al. |
| 11,357,738 B2 | 6/2022 | Meinert |
| 11,400,132 B2 | 8/2022 | Löscher et al. |
| 11,413,323 B2 | 8/2022 | Leo et al. |
| 11,576,893 B2 | 2/2023 | Löscher et al. |
| 11,583,513 B2 | 2/2023 | Günther et al. |
| 11,684,589 B2 | 6/2023 | Günther et al. |
| 11,723,861 B2 | 8/2023 | Günther et al. |
| 11,730,794 B2 | 8/2023 | Yancopoulos |
| 11,844,836 B2 | 12/2023 | Günther et al. |
| 11,896,559 B2 | 2/2024 | Günther et al. |
| 11,987,623 B2 | 5/2024 | Günther et al. |
| 12,005,033 B2 | 6/2024 | Günther et al. |
| RE50,060 E | 7/2024 | Graf et al. |
| 12,029,757 B2 | 7/2024 | Löscher et al. |
| 12,059,449 B2 | 8/2024 | Leo et al. |
| 12,128,010 B2 | 10/2024 | Scherer et al. |
| 12,150,955 B2 | 11/2024 | Loscher et al. |
| 12,226,422 B2 | 2/2025 | Löscher et al. |
| 2002/0004063 A1 | 1/2002 | Zhang |
| 2002/0006442 A1 | 1/2002 | Mishra et al. |
| 2002/0198266 A1 | 12/2002 | Meinert |
| 2003/0018044 A1 | 1/2003 | Peyman |
| 2003/0027833 A1 | 2/2003 | Cleary et al. |
| 2003/0170194 A1 | 9/2003 | Piotrowiak |
| 2004/0044045 A1 | 3/2004 | Burk |
| 2004/0082660 A1 | 4/2004 | Ueno |
| 2004/0101551 A1 | 5/2004 | Selzer |
| 2004/0265362 A1 | 12/2004 | Susilo |
| 2004/0266702 A1 | 12/2004 | Dawson |
| 2005/0075407 A1 | 4/2005 | Tamarkin et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0009522 A1 | 1/2006 | Dana et al. |
| 2006/0013820 A1 | 1/2006 | Bonnet et al. |
| 2006/0078580 A1 | 4/2006 | Dechow |
| 2006/0153905 A1 | 7/2006 | Carrara et al. |
| 2007/0249730 A1 | 10/2007 | Daftary et al. |
| 2008/0019926 A1 | 1/2008 | Krafft et al. |
| 2008/0050335 A1 | 2/2008 | Faour et al. |
| 2008/0089923 A1 | 4/2008 | Burkstrand et al. |
| 2008/0112895 A1 | 5/2008 | Kottayil et al. |
| 2008/0207537 A1 | 8/2008 | Turner et al. |
| 2008/0234389 A1 | 9/2008 | Mecozzi et al. |
| 2008/0254106 A1 | 10/2008 | Bell |
| 2008/0260656 A1 | 10/2008 | Mallard |
| 2009/0136430 A1 | 5/2009 | Dugger |
| 2009/0149546 A1 | 6/2009 | Chang |
| 2009/0169601 A1 | 7/2009 | Koch et al. |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0189765 A1 | 7/2010 | Erickson et al. |
| 2010/0210720 A1 | 8/2010 | Pilotaz et al. |
| 2010/0226997 A1 | 9/2010 | Bowman et al. |
| 2010/0274215 A1 | 10/2010 | Wong et al. |
| 2011/0223208 A1 | 9/2011 | Hill et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2013/0011484 A1 | 1/2013 | Bevier |
| 2013/0084250 A1 | 4/2013 | Hagedorn et al. |
| 2013/0309226 A1 | 11/2013 | Armstrong et al. |
| 2013/0336557 A1 | 12/2013 | Cruzat et al. |
| 2014/0004197 A1 | 1/2014 | Theisinger et al. |
| 2014/0186350 A1 | 7/2014 | Ghosh et al. |

(56) References Cited

U.S. PATENT DOCUMENTS

| | | |
|---|---|---|
| 2015/0045282 A1 | 2/2015 | Elsohly et al. |
| 2015/0099019 A1 | 4/2015 | Johnson |
| 2015/0174096 A1 | 6/2015 | Bottger et al. |
| 2015/0258040 A1 | 9/2015 | Lynch et al. |
| 2016/0000941 A1 | 1/2016 | Keller et al. |
| 2016/0184259 A1 | 6/2016 | Anastassov et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0224531 A1 | 8/2017 | Chauhan et al. |
| 2017/0348285 A1 | 12/2017 | Hellstron |
| 2018/0360908 A1 | 12/2018 | Beier et al. |
| 2019/0000919 A1 | 1/2019 | Brockmeyer et al. |
| 2019/0256591 A1 | 8/2019 | Günther et al. |
| 2019/0274970 A1 | 9/2019 | Günther et al. |
| 2019/0298801 A1 | 10/2019 | Kerwin et al. |
| 2019/0328717 A1 | 10/2019 | Günther et al. |
| 2019/0343793 A1 | 11/2019 | Günther et al. |
| 2020/0246463 A1 | 8/2020 | Günther et al. |
| 2021/0121471 A1 | 4/2021 | Löscher et al. |
| 2021/0315832 A1 | 10/2021 | Scherer et al. |
| 2021/0340248 A1 | 11/2021 | Günther et al. |
| 2021/0346313 A1 | 11/2021 | Beier et al. |
| 2022/0008397 A1 | 1/2022 | Xu et al. |
| 2022/0031844 A1 | 2/2022 | Mauden et al. |
| 2022/0079925 A1 | 3/2022 | Günther et al. |
| 2022/0143137 A1 | 5/2022 | Witt et al. |
| 2022/0152096 A1 | 5/2022 | Löscher et al. |
| 2022/0226427 A1 | 7/2022 | Leo et al. |
| 2022/0354786 A1 | 11/2022 | Friess et al. |
| 2022/0354926 A1 | 11/2022 | Löscher et al. |
| 2022/0362382 A1 | 11/2022 | Loscher et al. |
| 2022/0370377 A1 | 11/2022 | Scherer et al. |
| 2023/0043641 A1 | 2/2023 | Beier et al. |
| 2023/0139672 A1 | 5/2023 | Theisinger et al. |
| 2023/0181679 A1 | 6/2023 | Haisser et al. |
| 2023/0330056 A1 | 10/2023 | Günther et al. |
| 2023/0398065 A1 | 12/2023 | Günther et al. |

FOREIGN PATENT DOCUMENTS

| | | | |
|---|---|---|---|
| CN | 103096934 A | 5/2013 | |
| CN | 203524843 U | 4/2014 | |
| EP | 0 670 159 | 9/1995 | |
| EP | 1 152 749 | 11/2001 | |
| EP | 2708228 A1 | 3/2014 | |
| EP | 2730291 A1 | 5/2014 | |
| JP | S6452722 | 2/1989 | |
| JP | 2001/158734 | 6/2001 | |
| JP | 2011/006348 | 1/2011 | |
| JP | 2011/024841 | 2/2011 | |
| WO | WO 93/00991 | 1/1993 | |
| WO | WO 1998/005301 | 12/1998 | |
| WO | WO 00/54588 | 9/2000 | |
| WO | WO 2003/099258 | 12/2003 | |
| WO | WO 2007/149334 | 12/2007 | |
| WO | WO 2010/146536 | 12/2010 | |
| WO | WO 2011/112669 A1 | 9/2011 | |
| WO | WO 2012/097019 | 7/2012 | |
| WO | WO-2015011199 A1 * | 1/2015 | ........... A61K 39/395 |
| WO | WO 2016/082644 A1 | 6/2016 | |
| WO | WO 2016/208989 | 6/2016 | |
| WO | WO-2016208989 A1 * | 12/2016 | ........... A61K 38/179 |
| WO | WO 2017/120601 A1 | 7/2017 | |
| WO | WO-2017220625 A1 * | 12/2017 | ........... A61F 9/0008 |
| WO | WO-2018094316 A1 * | 5/2018 | ........... A61K 38/179 |

OTHER PUBLICATIONS

Meinert, Eur J Ophthalmol. 2000; 10(3):189-197, Abstract (Year: 2000).*

Agarwal et al., Int J Pharm. Mar. 1, 2018;538(1-2):119-129 (Year: 2018).*

"EvoTears, Product Description" Accessed Online: Dec. 21, 2023. https://evotears.com/at/das-produkt/ (Year: 2017).

"EvoTears—Gebrauchsanweisung," May 2015, retrieved from the Internet, date retrieved: Jun. 26, 2018, 2 pages, URL: http://video.apo-rot.de/docs/11213615.pdf.

"Novaliq Announces Positive Topline Results of Phase 2 Clinical Trial Evaluating CyclASol® in Adults with Moderate to Severe Dry Eye Disease," Businesswire, Jan. 5, 2017, URL: < https://www.businesswire.com/news/home/20170105005211/en/Novaliq-Announces-Positive-Topline-Results-Phase-2>.

"Novaliq begins Phase 2 trial of Cyclasol for dry eye disease," Optometry Times, vol. 8, No. 3, (2016), p. 24.

"Semifluorinated alkane technology brings advantages for topical therapy," Ophthalmology Times, 2016, pp. 1-2.

"Topical drug dosage forms for eye conditions," The Pharmaceutical Journal, (Pharmaceutical Press, May 31, 2017), available at https://pharmaceutical-journal.com/article/ld/topical-drug-dosage-forms-for-eye-conditions.

Ahmed, S. et al., "Ocular Drug Delivery: a Comprehensive Review," AAPS PharmSciTech, vol. 24, No. 66, pp. 1-29, (2023).

Chen, M. et al., "Persistent Inflammation Subverts Thrombospondin-1-Induced Regulation of Retinal Angiogenesis and Is Driven by CCR2 Litigation," The American Journal of Pathology, vol. 180, pp. 235-245, (2012).

Eva M. del Amo, "Topical ophthalmic administration: Can a drug instilled onto the ocular surface exert an effect at the back of the eye?" Frontiers in Drug Discovery 2:954771 (Sep. 8, 2022), available at https://www.frontiersin.org/articles/10.3389/fddev.2022.954771/full.

Kumar, S. et al., "Reduction in drop size of ophthalmic topical drop preparations and the impact of treatment," J. Adv. Pharm. Tech. Res., vol. 2, No. 3, (2011).

Messmer, E. et al., "Semifluorinated Alkanes as a Therapy for Meibomian Gland Dysfunction Results of a prospective, multi-centered observational study," Presentation, DOG-Kongress, Sep. 29, 2016-Oct. 2, 2016, Berlin DOG (Deutsche Ophtalmologische Gesellschaft), Ophtalmologe, Aug. 2016, Poster No. PSa03-02, English Translation of Abstract, p. 138.

Sheppard, J. et al., "A Water-free 0.1% Cyclosporine A Solution for Treatment of Dry Eye Disease: Results of the Randomized Phase 2B/3 Essence Study," Cornea, vol. 40, No. 10, pp. 1290-1297, (2021).

Steven, P. et al., "Semifluorinated Alkane Eye Drops for Treatment of Dry Eye Disease—A Prospective, Multicenter Noninterventional Study" Investigative Ophthalmology & Visual Science, vol. 56, No. 4493, 1 page, (2015), Abstract Only.

Torkildsen, G. et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans 2017.

Wu, Y. et al., "Tetramethylpyrazine (TMP) ameliorates corneal neovascularization via regulating cell infiltration into cornea after alkali burn," Biomedicine and Pharmacotherapy, vol. 109, pp. 1041-1051, (2018).

Guirakhoo et al., "Cloning, expression and functional activities of a single chain antibody fragment directed to fusion protein of respiratory syncytial virus," Immunotechnology 2(3): 219-228 (1996), Abstract only.

He et al., "High-throughput dynamic light scattering method for measuring viscosity of concentrated protein solutions," Analytical Biochemistry, 399(1): 141-143 (2010), Abstract only.

Kerns et al., Drug-Like Properties: Concepts, Structure Design and Methods: from ADME to Toxicity Optimization, 2008, Elsevier, Chapter 10, Section 10.4.3, 133, 2008, 2 parts.

Yaoxue Zhuanye Zhishi II (Editor: Jin Xiangqun), Military Medical Science Press, $1^{st}$ Printing of $2^{nd}$ Edition, Mar. 2009, p. 158.

Yaoxue Zhuanye Zhishi II (Editor: Jin Xiangqun), Military Medical Science Press, $1^{st}$ Printing of $2^{nd}$ Edition, Mar. 2009, p. 158, 3 pages (English Machine Translation).

(56) References Cited

OTHER PUBLICATIONS

Agarwal, P. et al., "Semifluorinated alkane based systems for enhanced corneal penetration of poorly soluble drugs," International Journal of Pharmaceutics, vol. 538, No. 1-2, pp. 119-129, (2018).
Augustin, A. et al., "Treatment of neovascular age-related macular degeneration: Current therapies," Clinical Ophthalmology, vol. 3, pp. 175-182, (2009).
Pensyl, D., "Chapter 14: Preparations for Dry Eye and Ocular Surface Disease," Clinical Ocular Pharmacology, Fifth Edition, pp. 263-278, 18 pages, (2008).
Schmitt, M., "Chapter 10: Design and Development of Ocular Formulations for Preclinical and Clinical Trials," Innovative Dosage Forms: Design and Development at Early Stage, pp. 331-365, 35 pages, (2020).
Turgut, B. et al., "The Impact of Tacrolimus on Vascular Endothelial Growth Factor in Experimental Corneal Neovascularization," Current Eye Research, vol. 36, No. 1, pp. 34-40, (2011).
Agarwal et al., "Modern Approaches to the Ocular Delivery of Cyclosporine A," Drug Discovery Today, vol. 21, No. 6, pp. 977-988, (2016); doi: 10.1016/j.drudis.2016.04.002.
Agrahari, et al., "A comprehensive insight on ocular pharmacokinetics," Drug Delivery and Translational Research, 6(6):735-754 (2016).
Ahmed, et al., "Disposition of Timolol and Inulin in the Rabbit Eye Following Corneal Versus Non-Corneal Absorption," International Journal of Pharmaceutics, 1987, 38:9-21.
Al-Amri, et al., "Long-term use of 0.003% tacrolimus suspension for treatment of vernal keratoconjunctivitis," Oman Journal of Ophthalmology, 10(3):145-149, (2017).
Astellas Pharma US, Inc. (2019). PROGRAF(R); Highlights of Prescribing Information. Northbrook, IL: Astellas Pharma US, Inc.
Baerdemaeker, "Pharmacokinetics in Obese Patients," Continuing Education in Anesthesia, Critical Care & Pain, 2004, 4:152-155.
Barata-Vallejo et al., "$(Me_3Si)_3SiH$-Mediated Intermolecular Radical Perfluoroalkylation Reactions of Olefins in Water," J. Org. Chem., 2010, 75:6141-6148.
Bardin et al., "Long-Range Nanometer-Scale Organization of Semifluorinated Alkane Monolayers at the Air/Water Interface," Langmuir, 2011, 27:13497-13505.
Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.
Blackie et al., "MGD: Getting to the Root Cause of Dry Eye," Review of Optometry, 2012, pp. 1-12.
Broniatowski, M. et al., "Langmuir Monolayers Characteristics of (Perfluorodecyl)-Alkanes," Journal of Physical Chemistry B, 2004, 108:13403-13411.
Cabral et al., "Retinal and choroidal angiogenesis: a review of new targets," International Journal of Retina and Vitreous, 2017, 3:31.
Chaglasian et al., "Recycling Cyclosporine," Review of Cornea & Contact Lenses, 5 pages, (2016).
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.
Chemical Book, 5-Fluorouracil, available at <http://www.chemicalbook.com/ChemicalProductProperty_EN_CB8162744.htm>, accessed Mar. 7, 2014, 1 page.
Chhadva et al., "Meibomian Gland Disease The Role of Gland Dysfunction in Drye Eye Disease," Ophthalmology (2017) 124(11 Supplement): S20-S26.
Costa Gomes et al., "Solubility of dioxygen in seven fluorinated liquids," Journal of Fluorine Chemistry, 2004, 125:1325-1329.
Davies, "Biopharmaceutical Considerations in Topical Ocular Drug Delivery," Clin. Exper. Pharmacol. Physiol., 2000, 27:558-562.
Dembinski et al., Semi-fluorinated Alkanes as Carriers for Drug Targeting in Acute Respiratory Failure, Experimental Lung Research, 2010, 36(8):499-507.
Dias et al., "Solubility of oxygen in liquid perfluorocarbons," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
Elkeeb, R. et al., "Transungual Drug Delivery: Current Status," International Journal of Pharmaceutics, 2010, 384:1-8.
English-language machine translation of EP0670159 (A1) issued in U.S. Appl. No. 14/122,025 on Apr. 1, 2015, 10 pages.
Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.
Garritty, James, "Blepharitis-17. Eye Diseases-MSD Manual Professional Edition," 3 pages, (2016); https://www.msdmanuals.com/ja-jp/プロフェッショナル/17-眼疾患//
眼瞼および流涙疾患/眼瞼炎.
Gayton, J., "Etiology, Prevalence, and Treatment of Dry Eye Disease," Clinical Ophthalmology, 2009, 3:405-412.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).
Gerdenitsch, "Emulsions—established and promising drug carriers for parenteral administration," retrieved from Internet, date accessed: Jun. 20, 2016, 2 pages URL: <http:/ipimediaworld.com/wp-content/uploads/2012/05/Pages-from-IPI-Volume-2-Issue-1-11.pdf.>.
German, E.J., et al., "Reality of drop size from multi-dose eye drop bottles: is it cause for concern?" Eye, 1999, 13:93-100.
Gopal et al., "Use of intravitreal injection of triamcinolone acetonide in the treatment of age-related macular degeneration," Indian J Ophthalmol., 2007, 55(6):431-435, (8 pages).
Griffin, W., "Classification of Surface-Active Agnets by 'HLB'," Journal of the Society of Cosmetic Chemists, 1949, 1:311-326.
Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf et al., "Combined Use of Partially Fluorinated Alkanes, Perfluorocarbon Liquids and Silicone Oil: An Experimental Study," Graefe's Archive For Clinical And Experimental Ophthalmology, 2001, 239(5):373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
Ishizaki et al., "Treatment of Diabetic Retinopathy," Forum: Complication, Practice, 2009, 26(5):474-476 (3 pages).
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
JPS6452722, English Machine Translation of the Abstract, Description, and Claims, Espacenet, Date Accessed: Feb. 10, 2016, 4 pages.
Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

(56) References Cited

OTHER PUBLICATIONS

Kheirkhah, A., et al., "Topical 0.005% tacrolimus eye drop for refractory vernal keratoconjunctivitis," Eye (London, England), 25(7):872-880, (2011).
Knepp et al., "Stability of Nonaqueous Suspension Formulations of Plasma Derived Factor IX and Recombinant Human Alpha Interferon at Elevated Temperatures," Pharmaceutical Research, 1998, 15(7):1090-1095.
Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lemp, M., "Management of Dry Eye Disease," The American Journal of Managed Care, 2008, 14(3):S88-S101.
Lin, H. et al., "Dry eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4):1873-1883.
Matteucci et al., "Biocompatibility assessment of liquid artificial vitreous replacements: relevance of in vitro studies," Survey of Ophthalmology, 2007, 52(3):289-299, Abstract Only (1 page).
Meinert, H. et al., "The Use of Semifluorinated Alkanes in Blood-Substitutes," Biomaterials, Artificial Cells, and Immobilization Biotechnology, 1993, 21 (5):583-595.
Meinert, H. et al., "Semifluorinated Alkanes—A New Class of Compounds with Outstanding Properties for Use in Ophthalmology," European Journal of Ophthalmology, 2000, 10 (3), 189-197.
Messmer, E.M., "The Pathophysiology, Diagnosis, and Treatment of Dry Eye Disease," (2015) Deutsches Arzteblatt International, 112(5):71-82.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Moscovici, et al., "Clinical treatment of dry eye using 0.03% tacrolimus eye drops," Cornea, 31(8):945-949, (2012).
Murdan, S., "Enhancing the Nail Permeability of Topically Appied Drugs," Expert Opinion on Drug Delivery, 2008, 5 (11):1267-1282.
Neely, K. et al., "Ocular Neovascularization: Clarifying Complex Interactions," American Journal of Pathology, 1998, vol. 153, No. 3.
Novaliq GmbH Begins Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.
Ohashi, et al., "A randomized, placebo-controlled clinical trial of tacrolimus ophthalmic suspension 0.1% in severe allergic conjunctivitis," Journal of ocular pharmacology and therapeutics, 26(2):165-174 (2010).
O'Rourke, M. et al., "Enhancing Delivery of Topical Ocular Drops," Cataract & Refractive Surgery Today Europe, 2016, 2 pages.
Park et al., "Inhibitory Effect of Topical Aflibercept on Corneal Neovascularization in Rabbits," Cornea, 2015, 34(10):1303-7.
Perry, "Dry Eye Disease: Pathophysiology, Classification, and Diagnosis," The American Journal of Managed Care, 2008, 14(3):S79-S87.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, 1 page, abstract only.
Plassmann, M. et al., "Trace Analytical Methods for Semifluorinated n-Alkanes in Snow, Soil, and Air," Analytical Chemistry, 2010, 82(11):4551-4557.
Plassmann, M. et al., "Theoretical and Experimental Simulation of the Fate of Semifluorinated n-Alkanes During Snowmelt," Environmental Science & Technology, 2010, 44(17):6692-6697.
Rosca-Casian, O. et al., "Antifungal Activity of Aloe vera Leaves," Fitoterapia, 2007, 28, 219-222.
Rosenberg, A., "Effects of Protein Aggregates: An Immunologic Perspective," The AAPS Journal, 2006, 8 (3), E501-E507.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Sella et al., "Efficacy of topical aflibercept versus topical bevacizumab for the prevention of corneal neovascularization in a rat model," Experimental Eye Research, 2016, 146:224-32.
Scherer et al., "Eyesol: A Novel Topical Ocular Drug Delivery System for Poorly Soluble Drugs," Drug Development & Delivery, vol. 13, No. 1, pp. 40-44, (2013).
Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.
Schnetler et al., "Lipid composition of human meibum: a review," S Afr Optom, 2013, 72(2), 86-93.
Spöler et al., "Towards a New in vitro Model of Dry Eye: The ex vivo Eye Irritation Test," Developments in Ophthalmology, 2010, 45, 93-107.
Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Stevenson, C., "Characterization of Protein and Peptide Stability and Solubility in Non-Aqueous Solvents," Current Pharmaceutical Biotechnology, 2000, 1, 165-182.
Tamura et al., "Tacrolimus is a class II low-solubility high-permeability drug: The effect of P- glycoprotein efflux on regional permeability of tacrolimus in rats," Journal of Pharmaceutical Sciences, 2002, 91(3):719-729 (Abstract Only), 1 page.
Tiffany, J.M., "Individual Variations in Human Meibomian Composition," Exp. Eye Res., 1978, 27, 289-300.
Tobe, T. et al., "Targeted Disruption of the FGF2 Gene Does Not Prevent Choroidal Neovascularization in the Murine Model," American Journal of Pathology., 1998, 153(5): 1641-1646.
Toma, H. S., "Improved assessment of laser-induced choroidal neovascularization," Microvasc. Res., 2010, 80(3): 295-302.
Troiano et al., "Effect of Hypotonic .4% Hyaluronic Acid Drops in Dry Eye Patients: A Cross-Study," Cornea 27(10): 1126-1130, 1 page (Abstract Only). 2008.
Wang, W., "Lyophilization and Development of Solid Protein Pharmaceuticals," International Journal of Pharmaceutics, 2000, 203, 1-60.
Wegewitz et al., "Novel Approaches in the Treatment of Angiogenic Eye Disease," Current Pharmaceutical Design, 2005; 11(18):2311-30 (Abstract Only).
"What is retinal vitrectomy?" Presented by: Medical Online, Obesity and Diabetes Mellitus, 2005, 4(2): 284-286 (3 pages).

(56) References Cited

OTHER PUBLICATIONS

Wirta, David L. et al., "A Clinical Phase II Study to Assess Efficacy, Safety and Tolerability of Waterfree Cyclosporine Formulation for the Treatment of Dry Eye Disease," Ophthalmology 126:792-800 (2019).

Wong et al., "Perfluorocarbons and Semifluorinated Alkanes," Seminars in Ophthalmology; vol. 15 (1), 2000, p. 25-35.

Wu et al., "Physicochemical characterization and aerosol dispersion performance of organic solution advanced spray-dried cyclosporine A multifunctional particles for dry powder inhalation aerosol delivery," International Journal of Nanomedicine, 2013, 8:1269-1283.

Wu, Y. et al., "Tetramethylpyrazine (TMP) ameliorates corneal neovascularization via regulating cell infiltration into cornea after alkali burn," Biomedicine and Pharmacotherapy, 2018, vol. 109, pp. 1041-1051.

Xalatan, Latanoprost Ophthalmic Solution, 50 μg/mL Prostaglandin $F_{2\alpha}$ analogue, Product Monograph, Jul. 21, 2014, 30 pages.

Yazu, et al., "The efficacy of 0.1% tacrolimus ophthalmic suspension in the treatment of severe atopic keratoconjunctivitis," Annals of allergy, asthma & immunology, 122(4), 387-392 (2019).

Zhang et al., "Surface micelles of semifluorinated alkanes in Langmuir-Blodgett monolayers," Phys. Chem. Chem. Phys., 2004, 6:1566-1569.

\* cited by examiner

SEQUENCE LISTING

<160> NUMBER OF SEQ ID NOS: 3

<210> SEQ ID NO 1
<211> LENGTH: 431
<212> TYPE: PRT
<213> ORGANISM: Artificial Sequence
<220> FEATURE:
<223> OTHER INFORMATION: Fc-fusion polypeptide

<400> SEQUENCE: 1

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
```

```
                    355                 360                 365
Asn Gly Gln Pro Glu Asn Asn Tyr Lys Thr Thr Pro Pro Val Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430

<210> SEQ ID NO 2
<211> LENGTH: 214
<212> TYPE: PRT
<213> ORGANISM: Artificial Sequence
<220> FEATURE:
<223> OTHER INFORMATION: recombinant humanized monoclonal antibody light
      chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 453
<212> TYPE: PRT
<213> ORGANISM: Artificial Sequence
<220> FEATURE:
<223> OTHER INFORMATION: recombinant humanized monoclonal antibody heavy
      chain

<400> SEQUENCE: 3

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
            35                  40                  45
Gly Trp Ile Asn Thr Tyr Thr Gly Glu Pro Thr Tyr Ala Ala Asp Phe
 50                  55                  60
Lys Arg Arg Phe Thr Phe Ser Leu Asp Thr Ser Lys Ser Thr Ala Tyr
 65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
                100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
            130                 135                 140
Thr Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
            290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
            370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
```

```
Val Met His Glu Ala Leu His Asn His Tyr Thr Gln Lys Ser Leu Ser
        435                 440                 445

Leu Ser Pro Gly Lys
    450
```

COMPOSITIONS AND METHODS FOR THE TREATMENT OF OCULAR NEOVASCULARIZATION

CROSS-REFERENCE TO RELATED APPLICATIONS

This application is a U.S. National Stage application under 35 U.S.C. § 371 of International Application No. PCT/EP2020/053405, filed on Feb. 11, 2020, which claims priority to and the benefit of European Application No. 19156934.2, filed on Feb. 13, 2019, and European Application No. 19171487.2, filed on Apr. 29, 2019, the contents of each of which are hereby incorporated by reference in their entireties.

BACKGROUND OF THE INVENTION

Neovascularization can occur in many eye diseases and its epidemiologic impact is significant. Ocular neovascularization is known from various parts of the eye, including the cornea, iris, retina, and choroid.

Corneal neovascularization is characterized by the invasion of new blood vessels into the cornea from the limbus. It is caused by a disruption of the balance between angiogenic and antiangiogenic factors that preserves corneal transparency. Advanced stages, in which ingrown blood vessels reach the visual axis, can become permanently vision-threatening and, in patients with corneal grafts, may contribute to rejection.

Several medical approaches, all of which are used off label, are available for treating corneal neovascularization. Recent studies involving monoclonal anti-VEGF antibodies have shown promising results for the reduction of corneal neovascularization. Topical and/or subconjunctival administration of bevacizumab or ranibizumab has demonstrated good short-term safety and efficacy although long-term data are lacking. Anti-VEGF therapy for corneal neovascularization is still considered experimental and off label, special consents are required, and insurance coverage may be denied. In case of cornea transplants, corneal neovascularization greatly elevates the risk of graft rejection and, ultimately, failure in patients undergoing corneal transplants.

The following documents discuss the use of anti-VEGF proteins in the treatment of corneal neovascularization.

U.S. Pat. No. 7,608,261 describes aqueous solutions of anti-VEGF protein that upon injection inhibit injury-induced corneal neovascularization WO2007/149334 describes the stability of aqueous ophthalmic formulations of anti-VEGF proteins.

WO2016/208989 describes aqueous solutions of anti-VEGF proteins that are characterized by high stability, e.g. for long term storage.

Park et al (Cornea. 2015; 34(10):1303-7) show that the topical administration of aqueous 0.1% aflibercept or 0.1% bevacizumab have comparable inhibitory effects on corneal neovascularization in rabbits.

Sella et al. (Exp Eye Res. 2016; 146:224-32) compare the inhibitory effect on corneal neovascularization using topical administration of high-concentrated aqueous aflibercept and bevacizumab formulations in a in a rat model of chemical burn.

WO2015/011199 describes compositions comprising an antigen-binding protein, and a liquid vehicle comprising a semifluorinated alkane.

SUMMARY OF THE INVENTION

The present invention is in the field of ophthalmology. In particular, the present invention relates to methods and compositions for the treatment of ocular neovascularization, especially corneal neovascularization.

DETAILED DESCRIPTION OF THE INVENTION

Figure 1:
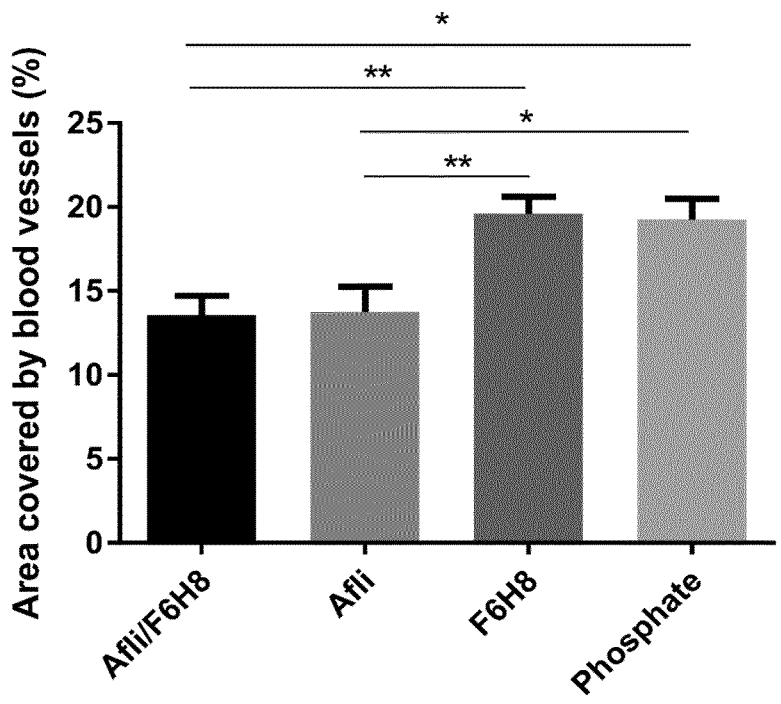
FIG. 1: Inhibition of blood vessel growth (hemeangiogenesis) in suture-induced inflammatory neovascularization mouse model utilizing the anti-VEGF protein aflibercept. Afli/F6H8=protein powder preparation of aflibercept suspended in 1-perfluorohexyloctane (F6H8) at a protein concentration of 5 mg/ml; Afli=aflibercept aqueous solution in 10 mM sodium phosphate buffer, pH 6.2 at a protein concentration of 5 mg/ml; F6H8=vehicle (1-perfluorohexyloctane); Phosphate=control (aqueous 10 mM sodium phosphate buffer, pH 6.2).

The invention is based on the finding of the inventors that ophthalmic compositions comprising particles of a powder preparation suspended in a liquid vehicle comprising a semifluorinated alkane, wherein the particles comprise an anti-VEGF-protein, are suitable for the treatment of ocular neovascularization.

As such, in a first aspect, the invention relates to a non-aqueous ophthalmic composition comprising particles suspended in a liquid vehicle comprising a semifluorinated alkane, wherein the particles comprise an anti-VEGF protein. Preferably, said particles are particles of a protein powder preparation.

In particular, the invention relates to a non-aqueous ophthalmic composition comprising particles of a protein powder preparation suspended in a liquid vehicle, wherein the particles of a protein powder preparation comprise an anti-VEGF protein and wherein the liquid vehicle comprises a semifluorinated alkane.

In the context of the present invention VEGF refers to Vascular endothelial growth factor. Vascular endothelial growth factor is a signal protein produced by cells that stimulates the formation of blood vessels (angiogenesis)

VEGF refers to a family of growth factors with several members. In mammals the family comprises VEGF-A to VEGF-D. Within the context of the present invention the term VEGF refers to any family member of the VEGF family.

In the context of the present invention, the term anti-VEGF protein refers to proteins that neutralize VEGF activity. In some embodiments, said anti-VEGF protein is an antigen binding polypeptide or protein that binds to a VEGF antigen. Polypeptides and proteins in general represent polymers of amino acid units that linked to each other by peptide bonds. Since the size boundaries that are often used to differentiate between polypeptides and proteins are somewhat arbitrary, the two expressions for these molecules should—within the context of the present invention—not be understood as mutually exclusive: A polypeptide may also be referred to as a protein, and vice versa. Typically, the term "polypeptide" only refers to a single polymer chain, whereas the expression "protein" may also refer to two or more polypeptide chains that are linked to each other by non-covalent bonds.

More specifically, and as used within the context of the present invention, antigen-binding polypeptides or proteins refer to full-length and whole antibodies (also known as immunoglobulins) in their monomer, or polymeric forms and any fragments, chains, domains or any modifications derived from a full-length antibody capable of specifically binding to an antigen. The antigen-binding polypeptides or proteins may belong to any of the IgG, IgA, IgD, IgE, or IgM immunoglobulin isotypes or classes. Fusion proteins comprising an antibody fragment capable of specifically binding to an antigen and antibody-drug conjugates are also within the definition of antigen-binding polypeptides or proteins as used herein.

A full-length antibody is a Y-shaped glycoprotein comprising of a general structure with an Fc (fragment crystallisable) domain and a Fab (fragment antigen binding) domain. These are structurally composed from two heavy (H) chains and two light (L) chain polypeptide structures interlinked via disulfide bonds to form the Y-shaped structure. Each type of chain comprises a variable region (V) and a constant region (C); the heavy chain comprises a variable chain region ($V_H$) and various constant regions (e.g. $C_H1$, $C_H2$, etc.) and the light chain comprises a variable chain region ($V_L$) and a constant region ($C_L$). The V regions may be further characterized into further sub-domains/regions, i.e. framework (FR) regions comprising more conserved amino acid residues and the hypervariable (HV) or complementarity determining regions (CDR) which comprise of regions of increased variability in terms of amino acid residues. The variable regions of the chains determine the binding specificity of the antibody and form the antigen-binding Fab domains of an antibody.

As used herein anti-VEGF proteins include, but are not limited to, anti-VEGF antibodies and related molecules. In a preferred embodiment of the invention, the compositions comprise an anti-VEGF protein, wherein the anti-VEGF protein is selected from a monoclonal antibody, polyclonal antibody, an antibody fragment, a fusion protein comprising an antibody fragment, an antibody-drug conjugate, or any combination thereof.

In a particularly preferred embodiment of the invention, the compositions comprise an anti-VEGF protein selected from a monoclonal antibody (mAb). A monoclonal antibody refers to an antibody obtained from a homogenous population of antibodies that are specific towards a single epitope or binding site on an antigen. Monoclonal antibodies may be produced using antibody engineering techniques known in the art, such as via hybridoma or recombinant DNA methods.

Also within the scope of anti-VEGF proteins are antibody fragments binding to a VEGF-antigen. Antibody fragments of the invention include any region, chain, domain of an antibody, or any constructs or conjugates thereof that can interact and bind specifically to a VEGF-antigen, and may be monovalent, bivalent, or even multivalent with respect to binding capability. Such antibody fragments may be produced from methods known in the art, for example, dissection (e.g. by proteolysis) of a full-length native antibody, from protein synthesis, genetic engineering/DNA recombinant processes, chemical cross-linking or any combinations thereof. Antibody fragments are commonly derived from the combination of various domains or regions featured in variable V region of a full-length antibody.

Preferably, the anti-VEGF protein of the present invention is selected from bevacizumab (Avastin), aflibercept (VEGF Trap-Eye; EYLEA®) and ziv-aflibercept (VEGF Trap; ZALTRAP®)

Aflibercept

Aflibercept (commercial name, EYLEA) is an anti-VEGF protein, namely a Fc-fusion polypeptide carrying extracellular domains of VEGF receptors, being used as decoy receptor to neutralize VEGF. Aflibercept is for treating patients suffering from Neovascular (Wet) Age-related Macular Degeneration (AMD), Macular Edema following Retinal Vein Occlusion (RVO), Diabetic Macular Edema (DME) and Diabetic Retinopathy (DR). The amino acid sequence of aflibercept (also known as VEGFR1 R2-FcAC1 (a)), as well as the nucleic acid sequence encoding the same, are set forth, e.g., in WO2012/097019.

The Protein sequence (SEQ ID NO: 1) for aflibercept is:

```
SDTGRPFVEMYSEIPEIIHMTEGRELVIPCRVTSPNITVTLKKFPLDTL

IPDGKRIIWDSRKGFIISNATYKEIGLLICEATVNGHLYKTNYLTHRQI

NTIIDVVLSPSHGIELSVGEKLVLNCTARTELNVGIDFNWEYPSSKHQH

KKLVNRDLKTQSGSEMKKFLSILTIDGVTRSDQGLYTCAASSGLMTKKN

STFVRVHEKDKTHTCPPCPAPELLGGPSVFLFPPKPKDTLMISRTPEVT

CVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDEL
```

-continued

TKNQVSLTCLVKGFYPSDIAVEWESNGQPENNYKTTPPVLDSDGSFFLY

SKLTVDKSRWQQGNVFSCSVMHEALHNHYTQKSLSLSPG

Ziv-Aflibercept

Ziv-aflibercept contains the same protein (active drug) as aflibercept but is specifically formulated for injection as an intravenous infusion. Ziv-aflibercept is not intended for ophthalmic use, as the osmolarity of the ziv-aflibercept preparation is significantly higher than that of intravitreal aflibercept injection. However, intravitreal ziv-aflibercept has been used with success for multiple ocular conditions with acceptable safety profile.

Bevacizumab

Bevacizumab is a recombinant humanized monoclonal antibody that blocks angiogenesis by inhibiting vascular endothelial growth factor A (VEGF-A). Bevacizumab is a full-length IgG1κ isotype antibody composed of two identical light chains (214 amino acid residues; SEQ ID NO: 2) and two heavy chains (453 residues; SEQ ID NO: 3) with a total molecular weight of 149 kDa. The two heavy chains are covalently coupled to each other through two inter-chain disulfide bonds, which is consistent with the structure of a human IgG1.

The protein sequence of the "Bevacizumab light chain" (SEQ ID NO: 2)

DIQMTQSPSSLSASVGDRVTITCSASQDISNYLNWYQQKPGKAPKVLIY

FTSSLHSGVPSRFSGSGSGTDFTLTISSLQPEDFATYYCQQYSTVPWTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

The protein sequence of the "Bevacizumab heavy chain" (SEQ ID NO: 3) is:

EVQLVESGGGLVQPGGSLRLSCAASGYTFTNYGMNWVRQAPGKGLEWVG

WINTYTGEPTYAADFKRRFTFSLDTSKSTAYLQMNSLRAEDTAVYYCAK

YPHYYGSSHWYFDVWGQGTLVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVICVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHNH

YTQKSLSLSPGK

As understood herein, anti-VEGF antibodies may be chimeric, humanized or human. Chimeric monoclonal antibodies, for example, refer to hybrid monoclonal antibodies comprising domains or regions of the heavy or light chains derived from antibody sequences from more than one species, for example from murine and human antibody sequences. Humanized monoclonal antibodies refer to those that are predominantly structurally derived from human antibody sequences, generally with a contribution of at least 85-95% human-derived sequences, whereas the term human refers to those are derived solely from human germline antibody sequences. In a preferred embodiment, the compositions comprise of an antigen-binding polypeptide or protein selected from a monoclonal antibody, wherein the monoclonal antibody is a chimeric, humanized, or human antibody.

The liquid vehicle comprises a semifluorinated alkane. Semifluorinated alkanes provide a number of advantages from the pharmaceutical perspective. They are substantially non-toxic and are found to be well-tolerated by various types of human and animal tissue when administered topically or parenterally. In addition, they are chemically inert and are generally compatible with active and inactive ingredients in pharmaceutical formulations. Semifluorinated alkanes, when acting as vehicles for compounds that are not soluble or poorly soluble (such as antigen-binding proteins or polypeptides), form dispersions or suspensions with very useful physical or pharmaceutical properties, i.e. with little or no tendency to form solid, non-dispersible sediments.

Semifluorinated alkanes are linear or branched alkanes some of whose hydrogen atoms have been replaced by fluorine. In the semifluorinated alkanes (SFAs) used in the present invention, one linear non-fluorinated hydrocarbon segment and one linear perfluorinated hydrocarbon segment are present. These compounds thus follow the general formula $F(CF_2)_n(CH_2)_mH$. According to the present invention, n is selected from the range of 3 to 12, and m is selected from the range of 3 to 12, preferably n is selected from the range of 4 to 8, and m is selected from the range of 4 to 10.

A nomenclature which is frequently used for semifluorinated alkanes designates a perfluorated hydrocarbon segment as RF and a non-fluorinated segment as RH. Alternatively, the compounds may be referred to as FnHm and FnHm, respectively, wherein F means a perfluorated hydrocarbon segment, H means a non-fluorinated segment, and n and m define the number of carbon atoms of the respective segment. For example, F3H3 is used for perfluoropropylpropane, $F(CF_2)_3(CH_2)_3H$. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferred semifluorinated alkanes include in particular the compounds F4H5, F4H6, F4H8, F6H4, F6H6, F6H8, and F6H10. Particularly preferred for carrying out the invention are F4H5, F4H6, F6H6 and F6H8. In another particularly preferred embodiment, the composition of the invention comprises F6H8.

Optionally, the composition may comprise more than one SFA. It may be useful to combine SFAs, for example, in order to achieve a particular target property such as a certain density or viscosity. If a mixture of SFAs is used, it is furthermore preferred that the mixture comprises at least one of F4H5, F4H6, F6H4, F6H6, F6H8, and F6H10, and in particular one of F4H5, F4H6, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFAs are chemically and physiologically inert, colourless and stable. Their typical densities range from 1.1 to 1.7 g/cm$^3$, and their surface tension may be as low as 19 mN/m. SFAs of the RFRH type are insoluble in water but also somewhat amphiphilic, with increasing lipophilicity correlating with an increasing size of the non-fluorinated segment.

The composition comprises a liquid vehicle, wherein the semifluorinated alkane is present at a concentration of at least 85% by weight of the composition (wt %), preferably the semifluorinated alkane is present at a concentration of about 85 to 99% by weight of the composition.

It has been found by the inventors that the presence of a semifluorinated alkane in a liquid vehicle or in particular as a liquid vehicle in a composition comprising an anti-VEGF protein has a remarkable stabilizing effect on anti-VEGF proteins. In particular, compositions comprising semifluorinated alkane as a liquid vehicle are capable of substantially preventing or inhibiting their aggregation and reducing chemical degradation over a substantial period of time, at room temperature and even at higher temperatures such as 40° C., without loss of biological activity. Furthermore, it has been found that a composition comprising an anti-VEGF protein and a liquid vehicle comprising a semifluorinated alkane shows anti-neovascularization activity when topically applied to the surface of the eye.

It has also been found that anti-VEGF protein dispersions and suspensions in semifluorinated alkanes exhibit a remarkable degree of physical stability. The occurrence of flotation or sedimentation takes place slowly, leaving sufficient time for the withdrawal of a dose after gentle shaking or swirling of the container (e.g. a vial) with the dispersion or suspension. The anti-VEGF protein particles in semifluorinated alkane appear to largely retain their original particle size distribution and are readily redispersible; poorly re-dispersible aggregates do not appear to be formed. Importantly, this provides for a higher level of dosing accuracy in terms of precision and reproducibility.

In contrast, suspensions or dispersions in other chemically inert vehicles tend to be unstable, leading to formation of dense and poorly redispersible aggregates, and making precise dosing challenging, or in some cases, impossible, such as leading to the clogging of fine-gauged needles typically used for subcutaneous injections. Aggregated protein particles also present a high risk towards triggering adverse immunogenic reactions.

The term protein powder preparation refers to a protein composition in powdered form, preferably it is in form of dry solid particles that comprise at least an anti-VEGF protein as defined above. The particles of the protein powder preparations may be obtained by lyophilization or by spray-drying from an aqueous solution comprising an anti-VEGF protein In a particular aspect, the invention therefore relates to an ophthalmic composition comprising particles of a protein powder preparation suspended in a liquid vehicle which comprises a semifluorinated alkane of the formula RFRH, wherein RF is a linear perfluorinated hydrocarbon segment with 4 to 8 carbon atoms, and wherein RH is a linear alkyl group with 4 to 10 carbons. Moreover, said particles of the protein powder preparation comprise an anti-VEGF protein. The particles of the protein powder preparation comprising an anti-VEGF protein are incorporated in the ophthalmic composition such as to form a suspension in the liquid vehicle.

The term liquid vehicle comprising a semifluorinated alkane refers to a liquid composition comprising at least one semifluorinated alkane. The liquid vehicle may comprise further compounds. Preferably, the liquid vehicle comprises one or more semifluorinated alkanes. More preferably, the liquid vehicle consists of at least one semifluorinated alkane or a mixture of semifluorinated alkanes.

Accordingly, in one embodiment, the invention relates to an ophthalmic composition comprising particles of a protein powder preparation suspended in a liquid vehicle, wherein the liquid vehicle consists of a semifluorinated alkane or a mixture of semifluorinated alkanes of formula $F(CF_2)$—$(CH_2)_mH$, wherein n is an integer from 4 to 8 and m is an integer from 4 to 10 and wherein the particles of the protein powder preparation comprise an anti-VEGF protein. In a particular embodiment, the liquid vehicle consists of a semifluorinated alkane of formula $F(CF_2)_n(CH_2)_mH$, wherein n is an integer from 4 to 8 and m is an integer from 4 to 10. In a preferred embodiment, said semifluorinated alkane or said mixture of semifluorinated alkanes is selected from at least one of F4H5, F4H6, F6H4, F6H6, F6H8, and F6H10, and in particular one of F4H5, F4H6, F6H6 and F6H8. In a specific embodiment the liquid vehicle consists of F6H8.

The anti-VEGF protein may be any suitable anti-VEGF protein as defined above. Preferably, the anti-VEGF protein is a fusion protein binding to VEGF. In one embodiment, the anti-VEGF protein comprises a sequence having at least 90% sequence identity to SEQ ID NO: 1. In one embodiment the anti-VEGF protein consists of a sequence having at least 90% sequence identity to SEQ ID NO: 1. In a further embodiment the, the anti-VEGF protein comprises a sequence having 100% sequence identity to SEQ ID NO. 1. In a further embodiment, the anti-VEGF protein consists of a sequence having 100% sequence identity to SEQ ID NO. 1. In a preferred embodiment the anti-VEGF protein is aflibercept or ziv-aflibercept.

In a further embodiment, the anti-VEGF protein is an antibody binding to VEGF. In one embodiment the anti-VEGF protein comprises a sequence having at least 90% sequence identity to SEQ ID NO: 2 or SEQ ID NO: 3. In a further embodiment, the anti-VEGF protein comprises protein sequences having at least 90% sequence identity to SEQ ID NO: 2 and SEQ ID NO: 3. In a particular embodiment, the anti-VEGF protein comprises at least two polypeptides, wherein each polypeptide consists of a sequence having at least 90% sequence identity to SEQ ID NO: 2 or of a sequence having at least 90% sequence identity to SEQ ID NO: 3. In some embodiments, the anti-VEGF protein consists of polypeptides comprising sequences having at 100% sequence identity to SEQ ID NO: 2 and SEQ ID NO: 3. In a further embodiment, the anti-VEGF protein consists of polypeptides consisting of sequences having at 100% sequence identity to SEQ ID NO: 2 and SEQ ID NO: 3. In a particular embodiment, the anti VEGF-protein is bevacizumab (avastin).

In some embodiments of the invention, the concentration of the anti-VEGF protein in the ophthalmic suspension of the present invention is up to about 60 mg/ml. In some embodiments, the concentration of the anti-VEGF protein in the ophthalmic suspension is in between about 1 to 60 mg/ml, preferably in between about 1 to 25 mg/ml, more probably between about 1 to 10 mg/ml, even more preferably the concentration of the anti-VEGF protein is about 5 mg/ml. In particular embodiments, the concentration of the anti-VEGF protein in the suspension is 60 mg/ml, 50 mg/ml, 40 mg/ml, 30 mg/ml, 20 mg/ml, 15 mg/ml, 10 mg/ml, 7.5 mg/ml, 5 mg/ml, 4 mg/ml, 3 mg/ml, 2.5 mg/ml, 2 mg/ml or 1 mg/ml.

The ophthalmic composition comprising particles suspended in a liquid vehicle may comprise any suitable amount of a protein powder preparation comprising an anti-VEGF-protein. The inventors found that the composition preferably comprises about up to 35% weight (wt %) of the protein powder preparation comprising an anti-VEGF-protein. As such, in one embodiment, the composition comprises up to about 35% by weight (wt %) of the protein powder preparation comprising an anti-VEGF-protein. In some embodiments the composition comprises between 0.1 and 16% by weight (wt5) of the protein powder preparation comprising an anti-VEGF-protein. In a preferred embodiment, the composition comprises between 0.5% and 8% by weight (wt %) of the protein powder preparation comprising an anti-VEGF-protein. In some embodiments, the composition comprises about 0.1%, 0.25%, 0.5%, 1.0%, 1.5%, 2.0%, 2.5%, 3.0%, 3.5%, 4.0%, 4.5%, 5.0% 6.0%, 7.0%, 7.5%, 8.0%, 9.0%, 10.0% 15.0%, 17.5%, 20.0%, 25%, 30%, 3 or 35.0% by weight (wt %) of the protein powder preparation comprising an anti-VEGF-protein. In a preferred embodiment, the composition comprises 1.0 to 4.0%, preferably about 1.2 or 3.8% by weight (wt %) of the protein powder preparation comprising an anti-VEGF-protein.

As noted before the particles of the protein powder preparation comprising an anti-VEGF protein may be obtained by lyophilization and/or spray drying. In some embodiments the particles of the protein powder preparation comprising an anti-VEGF protein are obtained by spray drying or lyophilization of an aqueous solution comprising an anti-VEGF protein. Said aqueous solution may further comprise protein stabilizing agents. Alternatively, or in addition, said aqueous solutions may comprise a buffering agent.

Suitable protein stabilizing agents and buffering agents are known to the skilled person. Preferably, said one or more protein stabilizing agents are selected from polyols, sugars (i.e. sucrose or trehalose), amino acids, amines and salting out salts, polymers, surfactants, and arginine.

Said buffering agent may be any pharmacologically acceptable buffering agent A preferred buffering agent is sodium phosphate.

In some embodiments, the particles of the protein powder preparation comprise an anti-VEGF protein and one or more protein stabilizing agents selected from polyols, sugars (i.e. sucrose or trehalose), amino acids, amines and salting out salts, polymers, surfactants, and arginine.

In a preferred embodiment of the invention, the particles of the protein powder preparation are obtained by lyophilization of an aqueous solution comprising an anti-VEGF protein, one or more protein stabilizing agents as defined above and a buffering agent. In a further preferred embodiment of the invention, the particles of the protein powder preparation are obtained by spry drying of an aqueous solution comprising an anti-VEGF protein, one or more protein stabilizing agents as defined above and a buffering agent. Preferably, said aqueous solution has a physiologically and pharmacologically acceptable pH. More preferably, said solution has an ophthalmologically acceptable pH.

Accordingly, in some embodiments, the invention relates to an ophthalmic composition comprising particles of a protein powder preparation suspended in a liquid vehicle comprising a semifluorinated alkane, wherein the particles of the protein powder preparation comprise an anti-VEGF protein, one or more protein stabilizing agents and optionally a buffering agent.

In a preferred embodiment said protein stabilizing agent is selected from polyols, sugars (i.e. sucrose or trehalose), amino acids, amines and salting out salts, polymers, surfactants, and arginine.

In a particular embodiment, the protein stabilizing agent is selected from sucrose, trehalose and polysorbate. In a preferred embodiment, said protein stabilizing agent is trehalose.

The total concentration of said particles in the ophthalmic composition according to the invention is up to 400 mg/ml. Preferably, the concentration of said particles in the ophthalmic composition is in between about 10 to 400 mg/ml, preferably between about 10 to 200 mg/ml, more preferably between 10 to 100 mg/ml, even more preferably between about 10 to 60 mg/ml.

Accordingly, in one embodiment, the invention relates to a composition as defined above, wherein the total solid content of the composition comprising the protein powder preparation suspended in the liquid vehicle comprising the semifluorinated alkane is in between about 10 to 400 mg/ml, preferably between about 10 to 200 mg/ml, more preferably between 10 to 100 mg/ml, even more preferably between about 10 to 60 mg/ml.

The invention further relates to a composition as defined above, wherein the size of 90% of the suspended particles of the protein powder preparation is between 1 to 100 μm, preferably it is between 1 to 50 μm, more preferably it is between 1 to 30 μm, even more preferably it is between 1 to 20 μm, as measured by laser diffraction.

It is a particular property of the invention that the anti-VEGF protein in the composition as defined above maintains its activity over storage, especially over a long period of time and even at elevated temperatures. The inventors found, that a composition as defined above, is able to stabilize an anti-VEGF protein in the absence of added preservative agents. As such, the invention relates, in some embodiments, to a composition as defined above, wherein the composition is free of a preservative.

In a particular embodiment, the invention relates to a composition as defined above wherein the anti-VEGF protein comprised in the suspension retains 90% of its activity when stored at 2-8° C. for up to 3 months or wherein the anti-VEGF protein comprised in the suspension retains 90% of its activity when stored at 25° C. and 60% humidity for up to 3 months. (see Example 2(c) stability)

In a further embodiment, the invention relates to a composition as defined above, wherein 90% of the suspended (anti-VEGF protein containing) particles retain their initial particle size when stored at 2-8° C. for up to 3 months or wherein 90% of the suspended (anti-VEGF protein containing) particles retain their initial particle size when stored at 25° C. and 60% humidity for up to 3 months.

In a preferred embodiment, the ophthalmic composition comprises anti-VEGF containing particles of a protein powder preparation suspended in a vehicle comprising F6H8, a protein stabilizing agent and a buffering agent.

In a further preferred embodiment, the ophthalmic composition comprises aflibercept containing particles of a protein powder preparation suspended in a vehicle comprising F6H8, sucrose and a buffering agent, wherein the concentration of aflibercept in the composition is about 5 mg/ml.

In a further preferred embodiment, the ophthalmic composition comprises bevacizumab containing particles of a protein powder preparation suspended in a vehicle comprising F6H8, trehalose and a buffering agent, wherein the concentration of bevacizumab in the composition is about 5 mg/ml.

The compositions of the invention are particularly suitable for medical uses, in particular ophthalmic uses. As such, in one embodiment, the invention relates to an ophthalmic composition as defined above in all embodiments for use as a medicament. In a further embodiment, the invention relates to an ophthalmic composition as defined above in all embodiments for use in the manufacture of a medicament.

The inventors surprisingly found, that a composition as defined above in all embodiments, i.e. a composition comprising a suspension of particles of a protein powder preparation (comprising an anti-VEGF protein) in a liquid vehicle comprising an SFA is as effective in the treatment of ocular neovascularization as an aqueous composition (solution) comprising said anti-VEGF protein.

As such, in a particular aspect, the invention relates to an ophthalmic composition comprising particles of a protein powder preparation suspended in a liquid vehicle comprising a semifluorinated alkane for use in a method for treatment and/or prevention of ocular neovascularization, wherein the protein powder preparation comprises an anti-VEGF protein. In a particular embodiment, the invention relates to an ophthalmic composition comprising particles of a protein powder preparation suspended in a liquid vehicle comprising a semifluorinated alkane for use the manufacture of a medicament for treatment and/or prevention of ocular neovascularization, wherein the protein powder preparation comprises an anti-VEGF protein.

In some embodiments, the invention relates to a composition as defined above in all embodiments for use in a method of treatment and/or prevention of ocular neovascularization. The invention further relates to the use of a composition as defined above in a method for treatment and/or prevention of ocular neovascularization.

The inventors found that compositions as defined above in all embodiments show an inhibition of blood vessel growth comparable or better than aqueous compositions comprising the same anti-VEGF protein. Accordingly, in a particular embodiment, the invention relates to a composition as defined above in all embodiments for use in a method of the inhibition of growth of blood vessels and/or lymphatic vessels. In some embodiments the invention relates to a composition as defined above in all embodiments for use in the manufacture of a medicament for use in a method of the inhibition of growth of blood vessels and/or lymphatic vessels.

In a particular embodiment of the invention, the invention relates to a composition as defined above in all embodiments for use in a method of the simultaneous inhibition of growth of blood vessels and lymphatic vessels. In some embodiments the invention relates to a composition as defined above in all embodiments for use in the manufacture of a medicament for use in a method of the simultaneous inhibition of growth of blood vessels and lymphatic vessels.

The compositions according to the invention are suitable to be used for the treatment of any type of ocular neovascularization and particularly suitable for the treatment and/or prevention of corneal neovascularization, in particular for the treatment, prevention and/or control of corneal angiogenesis and/or corneal lymphangiogenesis.

Accordingly, in one embodiment, the invention relates to a composition as defined above in all embodiments for use in a method of treatment and/or prevention of corneal neovascularization. In a further embodiment, the invention relates to a method as defined above in all embodiments for use in the manufacture of a medicament for the treatment and/or prevention or corneal neovascularization.

In a particular embodiment, the invention relates to a composition as defined above in all embodiments for use in a method of prevention and/or treatment of corneal angiogenesis and/or corneal lymphangiogenesis. In a further embodiment, the invention relates to the use of said compositions in a method of manufacture of a medicament for use in a method of prevention and/or treatment of corneal angiogenesis and/or corneal lymphangiogenesis.

The invention also relates to the use of compositions as defined above in all embodiments in a method of treatment or prevention of ocular neovascularization as defined above. In such a use, the composition is preferably applied to the eye or an ophthalmic tissue. More preferably, the composition as defined above is applied topically to the eye or an ophthalmic tissue.

As such, the composition and the application are particularly suitable for subjects or patients, which may be affected by neovascularization. Such subjects include patients about to or having received ophthalmic surgery, in particular corneal surgery, especially corneal transplantations.

The invention further relates to a method for treatment and/or prevention of ocular neovascularization comprising administering a composition as defined above in all embodiments to the eye or an ophthalmic tissue of a subject. In a particular embodiment, said method is a method for treatment and/or prevention of corneal neovascularization, especially treatment or prevention of corneal angiogenesis and/or corneal lymphangiogenesis.

The invention further relates to a method for inhibiting blood vessel and/or lymphatic vessel growth comprising administering a composition as defined above in all embodiments to the eye or an ophthalmic tissue of a subject.

In either method of the invention, the composition as defined herein, is preferably applied topically to the eye or ophthalmic tissue of a subject.

Said subject preferably is a vertebrate, more preferably a mammal. In some embodiments, the invention relates to a method as defined above, in all embodiments, wherein the subject is a mammal. In a particular embodiment, the subject is a human.

In some embodiments, the invention relates to a method as defined above, wherein the subject is at risk of being affected by or is affected by ocular neovascularization. In a particular embodiment, said subject has received or is receiving ophthalmic surgery, in particular corneal surgery. In a specific embodiment, the subject is receiving or has received corneal transplantation surgery.

In a further aspect the invention relates to a kit comprising an ophthalmic composition as defined herein in all embodiments and a container adapted for administration to the eye. In a preferred embodiment the container is adapted for topical application.

Preferably, said kit further comprises instructions for use.

The invention further relates in particular to the following numbered items:

1. A non-aqueous ophthalmic composition comprising particles suspended in a liquid vehicle comprising a semifluorinated alkane, wherein the particles comprise an anti-VEGF protein.
2. A non-aqueous ophthalmic composition according to item 1 comprising particles of a protein powder preparation suspended in a liquid vehicle comprising a semifluorinated alkane, wherein the particles of the powder preparation comprise an anti-VEGF protein.
3. The composition of item 1 or 2, wherein the anti-VEGF protein comprises a sequence having at least 90% sequence identity to SEQ ID NO: 1
4. The composition of item 1 to 3, wherein the anti-VEGF protein is selected from aflibercept and ziv-aflibercept
5. The composition of item 1 or 2, wherein the anti-VEGF protein comprises a sequence having at least 90% sequence identity to SEQ ID NO: 2 and SEQ ID NO: 3
6. The composition of item 1, 2 or 5, wherein the anti-VEGF protein is bevacizumab.

7. The composition according to any preceding item, wherein the particles are obtained by spray-drying or lyophilization of an aqueous anti-VEGF protein solution.
8. The composition according to item 7, wherein the concentration of the anti-VEGF protein in the aqueous anti-VEGF protein solution is in between about 1 to 60 mg/ml, preferably in between about 1 to 25 mg/ml, more preferably between about 1 to 10 mg/ml, even more preferably the concentration of the anti-VEGF protein is about 5 mg/ml.
9. The composition according to items 6 or 7, wherein the aqueous anti-VEGF protein solution comprises one or more protein stabilizing agents selected from polyols, sugars (i.e. sucrose or trehalose), amino acids, amines and salting out salts, polymers, surfactants, and arginine.
10. The composition according to any preceding item, wherein the particles of the protein powder preparation comprise one or more protein stabilizing agents selected from polyols, sugars (i.e. sucrose or trehalose), amino acids, amines and salting out salts, polymers, surfactants, and arginine suspended in the liquid vehicle
11. The composition according to any preceding item, wherein the particles of the protein powder preparation comprise a protein stabilizing agent selected from sucrose, trehalose and polysorbate.
12. The composition according to any preceding item, wherein the concentration of the anti-VEGF protein in the composition is in between about 1 to 60 mg/ml, preferably in between about 1 to 25 mg/ml, more preferably between about 1 to 10 mg/ml, even more preferably the concentration of the anti-VEGF protein is about 5 mg/ml.
13. The composition according to any preceding item, wherein the total solid content of the composition is in between about 10 to 400 mg/ml, preferably between about 10 to 200 mg/ml, more preferably between 10 to 100 mg/ml, even more preferably between about 10 to 60 mg/ml.
14. The composition according to any preceding item, wherein the size of 90% of the suspended particles of protein powder preparation is between 1 to 100 μm, preferably it is between 1 to 50 μm, more preferably it is between 1 to 30 μm, even more preferably it is between 1 to 20 μm, as measured by laser diffraction.
15. The composition according to any preceding item, wherein the semifluorinated alkane is of formula $F(CF_2)$—$(CH_2)_mH$, wherein n is an integer from 4 to 8 and m is an integer from 4 to 10.
16. The composition according to any preceding item, wherein the semifluorinated alkane is selected from F4H4, F4H5, F4H6, F6H4, F6H6, F6H8, F8H8.
17. The composition according to any preceding item, wherein the semifluorinated alkane is selected from 1-perfluorobutylpentane (F4H5) and 1-perfluorohexyloctane (F6H8), preferably the semifluorinated alkane is 1-perfluorohexyloctane (F6H8)
18. The composition according to any preceding item, wherein the semifluorinated alkane is present at a concentration of at least 85% by weight of the composition (wt %), preferably the semifluorinated alkane is present at a concentration of about 85 to 99% by weight of the composition.
19. The composition according to any preceding item, wherein the composition is free of a preservative.
20. The composition according to any preceding item, wherein the anti-VEGF protein comprised in the suspended particles retains 90% of its activity when the composition is stored at 2-8° C. for up to 3 months or wherein the anti-VEGF protein comprised in the suspended particles retains 90% of its activity when the composition is stored at 25° C. and 60% humidity for up to 3 months.
21. The composition according to any preceding item, wherein 90% of the suspended particles retain their initial particle size when the composition is stored at 2-8° C. for up to 3 months or wherein 90% of the suspended particles retain their initial particle size when the composition is stored at 25° C. and 60% humidity for up to 3 months.
22. The composition according to any of the preceding items, wherein the particles of the protein powder preparation are suspended in a vehicle comprising F6H8, sucrose and a buffering agent and wherein the composition comprises 5 mg/ml aflibercept
23. The composition according to any of the preceding items, wherein the particles of the protein powder preparation are suspended in a vehicle comprising F6H8, trehalose and a buffering agent and wherein the composition comprises 5 mg/ml bevacizumab
24. The composition according to any preceding items, for use as a medicament.
25. The composition for use according to item 24, in the prevention and/or treatment of ocular neovascularization.
26. The composition for use according to 24 to 25 in the inhibition of growth of blood vessels and/or lymphatic vessels.
27. The composition for use according to 24 to 26 in the simultaneous inhibition of growth of blood vessels and lymphatic vessels
28. The composition for use according to items 24 to 27, in the prevention and/or treatment of corneal neovascularization and/or corneal angiogenesis
29. The composition for use according to items 24 to 28, in the prevention and/or treatment of corneal angiogenesis and/or corneal lymphangiogenesis
30. The composition for use according to items 24 to 29, wherein the composition is topically administered to the eye or an ophthalmic tissue.
31. The composition for use according to 24 to 30, wherein the administration of the composition to a subject undergoing corneal transplantation.
32. A kit comprising an ophthalmic composition as defined in any of the items 1 to 23, a container for holding said composition adapted for administration to the eye or an ophthalmic tissue.
33. The kit of item 32, wherein the container is administered for topical administration.
34. A method for treating ocular neovascularization, comprising administering a composition according to any of the items 1 to 23 to the eye or an ophthalmic tissue.
35. The method according to any of the items 34, wherein the method is effective in inhibiting blood vessel and/or lymphatic vessel growth.
36. Use of a composition as defined in any of the items 1 to 23 for manufacture of a medicament for use in the treatment of ocular neovascularization.

37. A method for fabrication of a stable non-aqueous ophthalmic anti-VEGF-protein containing composition as defined in any of the items 1 to 23, comprising the steps of
(a) subjecting an aqueous solution comprising an anti-VEGF protein, and optionally a protein stabilizing agent and/or a buffering agent, to spray-drying or lyophilization to form particles of a protein powder preparation
(b) suspending the particles of said protein powder preparation in a liquid vehicle comprising a semifluorinated alkane to form the anti-VEGF protein containing composition

EXAMPLES

Example 1: Preparation of the Ophthalmic Compositions

Starting from the aqueous commercial protein raw material of aflibercept (Zaltrap; Sanofi Genezyme; comprising 25 mg/ml aflibercept and additionally sucrose as protein stabilizer) and bevacizumab (Avastin; Roche; comprising 25 mg/ml bevacizumab and furthermore trehalose as protein stabilizer) the ophthalmic suspensions of the present invention were prepared with the following steps:
(a) dilution of the aqueous commercial protein raw material to the desired concentration,
(b) protein powder preparation (i.e. via spray-drying or lyophilization) of the diluted aqueous protein raw material of (a) and
(c) preparation of the ophthalmic composition by suspending the protein powder preparations (b) in a liquid vehicle comprising a semifluorinated alkane (i.e. F6H8)
ad a) The concentrated aqueous aflibercept (25 mg/ml) and bevacizumab (25 mg/ml) protein solutions were diluted with 5 mM sodium phosphate buffer, pH 6.2, to obtain a total solid content of 4-5% (w/v).
ad b) The protein powder preparations comprising the anti-VEGF proteins (aflibercepts, bevacizumab) were e.g. prepared by spray-drying. Herein, the spray-drying was conducted using a Büchi B290 equipped with a high efficiency cyclone under the following conditions: Nozzle diameter 0.7 mm, drying air flow rate 35 m3/h, atomizing air flow rate 414 L/h. Obtained were protein powder preparations comprising aflibercept or bevacizumab.
ad c) The ophthalmic SFA-containing compositions were prepared by suspending the appropriate amount of protein powder preparations (i.e. ~50 mg of a aflibercept or ~15 mg of bevacizumab containing protein power preparation) in F6H8 by vortexing, followed by 20 min sonication in an ultrasound bath filled with ice water and intermittent vortexing (every 5 min) to receive 5 mg/ml aflibercept suspended in F6H8 (further comprising sucrose and buffering salts as protein stabilizer) and 5 mg/ml bevacizumab suspended in F6H8 (further comprising trehalose and buffering salts as protein stabilizer).

As reference material aqueous ophthalmic solutions of aflibercept and bevacizumab were prepared by diluting the 25 mg/ml aqueous commercial protein raw material in sterile 10 mM sodium phosphate buffer (pH 6.2) to the desired final protein concentration of 5 mg/ml for aflibercept and bevacizumab.

Example 2: Analysis of the Ophthalmic Compositions (a) Reconstituted water-based protein powder preparation
SEC-MALS (Size Exclusion Chromatography-Multi Angle Light Scattering) and ELISA was carried out on the aqueous commercial protein raw material (RM) of aflibercept and bevacizumab and the reconstituted protein powder preparation of aflibercept and bevacizumab to ensure that the manufacturing process did not change the protein. Herein, the reconstituted protein powder preparations (REP) of aflibercept and bevacizumab were obtained by extracting said anti-VEGF proteins from the non-aqueous SFA-based ophthalmic suspensions into water. In the extraction procedure equal volumes of water were added followed by gently shaking of the biphasic samples until the organic (semifluorinated alkane) phase becomes clear and all the anti-VEGF protein has moved into the aqueous phase. This aqueous layer (REP) was then transferred into a fresh vial and analysed for protein fragmentation/aggregation via SEC-MALS and for protein activity via ELISA. Protein aggregation and fragmentation Protein aggregation and fragmentation can be detected by first separating the fractions followed by determination of their molecular weight, i.e. SEC-MALS analysis.

SEC-MALS analysis revealed that the chromatograms of the aqueous commercial protein raw material (RM) and the reconstituted protein powder preparations (REP) of both aflibercept and bevacizumab overlap very well and did not show an increase in aggregated or fragmented species.

(b) Protein Activity
ELISA was used to evaluate the activity of both proteins which involves the binding to VEGF, thereby inhibiting angiogenesis. The test is based on sandwich-type ELISA using a microtiter plate coated with recombinant human VEGF-A. Horseradish peroxidase (HRP)-conjugated anti-human IgG monoclonal antibody, which bind to the Fc region of antibodies, is then employed to quantify the bound Aflibercept or Bevacizumab. Both assays were performed using commercial kits from ImmunoGuide according to the manufacturer's instructions utilizing aqueous commercial protein raw material (RM) and reconstituted protein powder preparations (REP).

The corresponding ELISA analyses also showed no significant difference in the binding activity between the RM and REP of both aflibercept and bevacizumab, therefore, the process of powder production as well as the subsequent preparation of the ophthalmic suspensions did not affect the activity of both anti-VEGF proteins (aflibercept, bevacizumab).

(c) Stability
Samples of the ophthalmic suspension of protein powder preparations of aflibercept and bevacizumab in F6H8 were prepared and placed on stability for three months. Two replicas were tested at each timepoint, initial, one month and 3 months. For the analysis of the stability samples, the anti-VEGF protein was extracted from the semifluorinated alkane-based ophthalmic suspension into the aqueous environment as described above.

This stability study revealed that ophthalmic suspension of protein powder preparations of aflibercept (Table 1) and bevacizumab (Table 2) in F6H8 are stable in respect to assay, activity and aggregation when stored at 2-8° C. and 25° C./60% RH.

TABLE 1

Stability study results aflibercept

| Temperature | Test | Method | Initial | 1 month | 3 months |
|---|---|---|---|---|---|
| 2-8° C. | Assay | UV - Absorption | 4.01 mg/ml | 4.11 mg/ml | 4.28 mg/ml |
|  | Activity | ELISA | 103.6% | n. t. | 90.8% |
|  | Aggregation | SEC-MALS | <LOD | 1.1% | 0.25% |
| 25° C./65% RH | Assay | UV - Absorption | 4.01 mg/ml | 4.19 mg/ml | 4.25 mg/ml |
|  | Activity | ELISA | 103.6% | n. t. | 96.5% |
|  | Aggregation | SEC-MALS | <LOD | 1.8% | 0.5% |

TABLE 2

Stability study results bevacizumab

| Temperature | Test | Method | Initial | 1 month | 3 months |
|---|---|---|---|---|---|
| 2-8° C. | Assay | UV - Absorption | 4.28 mg/ml | 4.23 mg/ml | 4.42 mg/ml |
|  | Activity | ELISA | 91.5% | 99.3% | 94.7% |
|  | Aggregation | SEC-MALS | 2.7% | 3.2% | 7.7% |
| 25° C./65% RH | Assay | UV - Absorption | 4.28 mg/ml | 4.20 mg/ml | 4.33 mg/ml |
|  | Activity | ELISA | 91.5% | 92.1% | 85.3% |
|  | Aggregation | SEC-MALS | 2.7% | 4.0% | 18.2% |

Example 3: Suture-Induced Inflammatory Corneal Neovascularization Assay

Animals (BALB/c mice) were anesthetized with an intramuscular injection of ketamine (8 mg/kg) and xylazine (0.1 mL/kg) followed by placement of three 11-0 nylon sutures intrastromally with two stromal incursions extending over 120° of corneal circumference each. The outer point of suture placement was chosen near the limbus, and the inner suture point was chosen near the corneal centre equidistant from the limbus, to obtain standardized angiogenic responses. Sutures were left in place for the duration of the experiment.

Following the surgical procedure, the mice were treated for 14 days, three times daily with 3 μl of control (buffer), ophthalmic compositions comprising protein powder preparation of bevacizumab and aflibercept suspended in F6H8 or blanks (10 mice per sample).

The tested ophthalmic anti-VEGF protein compositions included:

At the end of the treatment period, the animals were sacrificed, and their corneas analysed for the presence of blood and lymphatic vessels.

Example 4: Morphological Determination of Hemeangiogenesis and Lymphangiogenesis The animal corneas were excised, rinsed in PBS and fixed in acetone for 30 min. After three additional washing steps in PBS and blocking with 2% BSA in PBS for 2 h the corneas were stained overnight at 4° C. with rabbit anti-mouse LYVE-1. On day two the tissue was washed, blocked and stained with FITC-conjugated rat anti-CD31 (Acris Antibodies GmbH, Hiddenhausen, Germany) antibody overnight at 4° C. After a last washing and blocking step on day three, a goat-anti-rabbit Cy3-conjugated secondary antibody

| Anti-VEGF protein | Protein concentration | vehicle | composition | further composition components |
|---|---|---|---|---|
| aflibercept | 5 mg/ml | 10 mM sodium phosphate buffer, pH 6.2 | aqueous aflibercept solution | sucrose |
| aflibercept | 5 mg/ml | F6H8 | non-aqueous suspension of aflibercept protein powder preparation | sucrose |
| bevacizumab | 5 mg/ml | 10 mM sodium phosphate buffer, pH 6.2 | aqueous bevacizumab solution | trehalose |
| bevacizumab | 5 mg/ml | F6H8 | non-aqueous suspension of bevacizumab protein powder preparation | trehalose | was used. Isotype control was assured with an FITC-conjugated normal ratIgG2A for CD31/FITC and with a normal rabbit IgG (both Santa Cruz Biotechnology, Santa Cruz, CA, USA) for LYVE-1.

Double stained whole mounts were analysed with a fluorescence microscope (BX51, Olympus Optical Co., Hamburg, Germany) and digital grey value pictures were taken with a 12-bit monochrome CCD camera (F-View II, Soft Imaging System, Munster, Germany) at a resolution of 1376×1023 pixel. For the FITC stained blood vessels an HQ-FITC selectiv filterset (Exciter: HQ 480/40; Emitter: HQ 527/30; AHF Analysentechnik AG, Tübingen, Germany) was used. For the Cy3 stained lymphatic vessels the U-MWG2 mirror unit (Excitation filter: 510-550 nm; Emission filter: 590 nm; Dichromatic mirror: 570 nm; Olympus, Hamburg Germany) was used. Each whole mount picture was assembled out of 9 pictures taken at 100× magnification. The inhibition of blood vessel growth or lymph vessel growth are depicted in FIGS. 1 to 4.

Example 5: Early Effect

Figure 5:
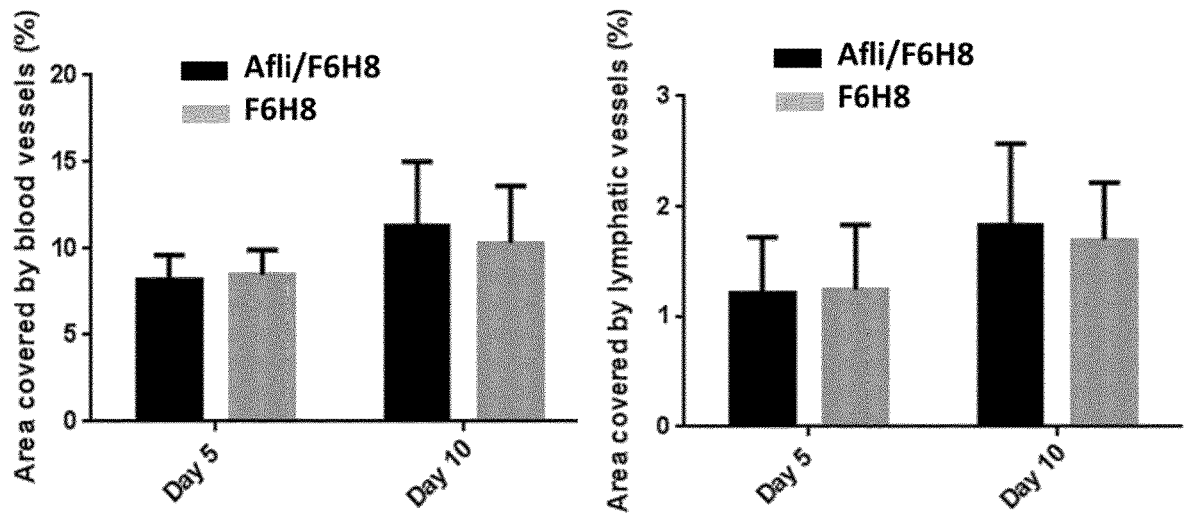
FIG. 5 Inhibition of blood vessel growth and lymph vessel growth in the suture-induced inflammatory neovascularization mouse model utilizing the anti-VEGF protein aflibercept at an early timepoint, namely after 5 and 10 days after suture induction (dosage regimen: 3-times daily, each 3 µl).

Six- to eight-week-old female BALB/c mice were used for the model of suture-induced inflammatory neovascularization. Three 11-0 nylon sutures were placed intrastromally on the right eye with two stromal incursions extending over 120 degrees of corneal circumference each. The outer point of suture placement was chosen near the limbus and the inner suture point was placed near the center of cornea equidistant from the limbus to obtain standardized angiogenic responses. Mice were divided into 2 groups (n=10): aflibercept suspended in semifluorinated alkanes (Afli/F6H8); aflibercept dissolved in Phosphate (Afli). Right after the suturing, drops were applied three times per day. Five and ten days after topical administration, corneas were harvested and stained with LYVE-1 and CD31 to quantify corneal hem- and lymphangiogenesis morphometric. FIG. 5 shows the early effect (5 days, 10 days) of inhibition of growth of both blood vessels and lymphatic vessels upon treatment with an ophthalmic composition comprising protein powder preparation of aflibercept suspended in F6H8 (Afli/F6H8). This effect is comparable to the aqueous aflibercept formulation (Afli).

Example 6: Low Dose Application

Figure 6:
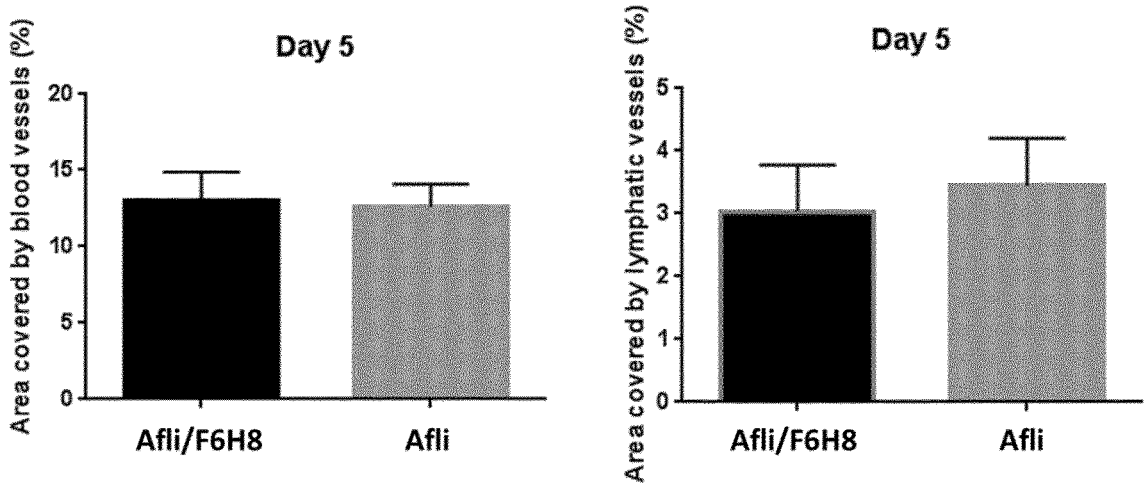
FIG. 6 Inhibition of blood vessel growth and lymph vessel growth in the suture-induced inflammatory neovascularization mouse model utilizing the anti-VEGF protein aflibercept utilizing a low dose application scheme (dosage regimen: 1-times daily; 3 µl) at an early timepoint after 5 days after suture induction.

The procedure is similar to Example 5, except for the treatment regime. Drops were applied only one time per day (3 μl) and corneas were harvested 5 days after topical application. FIG. 6 shows that the effect of inhibition of growth of both blood vessels and lymphatic vessels can be achieved also with a reduced dosage. Herein, treatment with an ophthalmic composition comprising protein powder preparation of aflibercept suspended in F6H8 (Afli/F6H8) shows a comparable effect when compared to the aqueous aflibercept formulation (Afli).

Example 7: Effect of Inflammatory Cells

Figure 7:
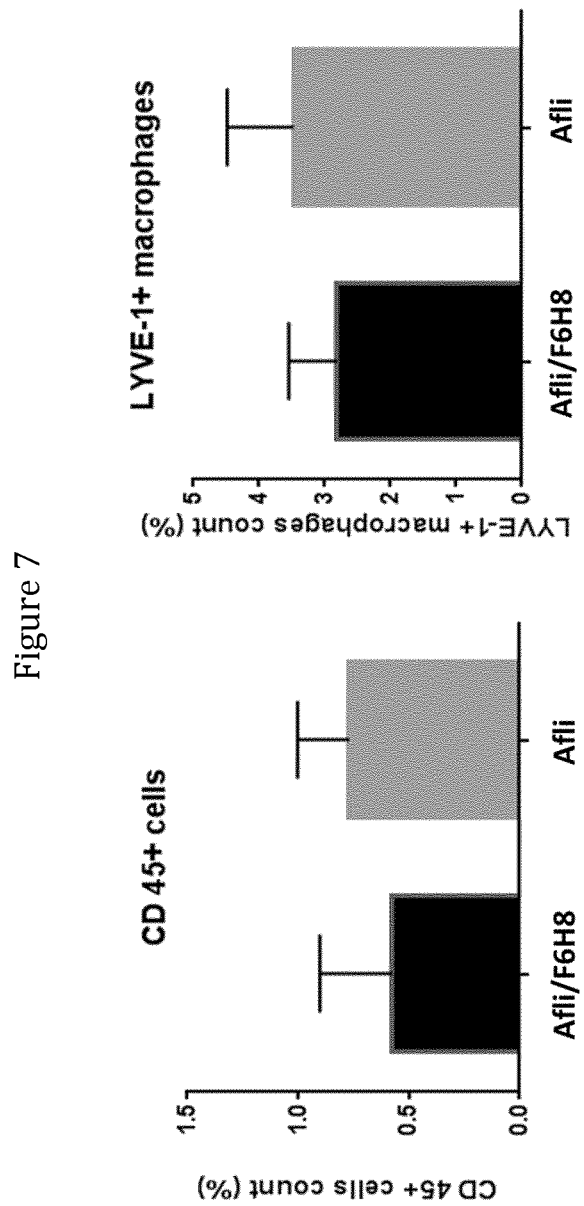
FIG. 7 Infiltration of inflammatory cells such as CD45+ cells and LYVE-1 macrophages at the early timepoint after 3 days after suture induction.

Six- to eight-week-old female BALB/c mice were used for the model of suture-induced inflammatory neovascularization. Three 11-0 nylon sutures were placed intrastromally on the right eye with two stromal incursions extending over 120 degrees of corneal circumference each. The outer point of suture placement was chosen near the limbus and the inner suture point was placed near the center of cornea equidistant from the limbus to obtain standardized angiogenic responses. Mice were divided into 2 groups (n=10): aflibercept suspended in semifluorinated alkanes (Afli/F6H8); aflibercept dissolved in Phosphate (Afli). Right after the suturing, drops were applied three times per day. Three days after topical administration, corneas were harvested and stained with LYVE-1 and CD45 to quantify CD45+ cells and LYVE-1 macrophages. FIG. 7 shows the infiltration of inflammatory cells such as CD45+ cells and LYVE-1 macrophages at the early phase after 3 days. It appears that the ophthalmic composition comprising protein powder preparation of aflibercept suspended in F6H8 (Afli/F6H8) relates to slightly less infiltration of inflammatory cells when compared to the aqueous aflibercept formulation (Afli).

FIG. 1 shows the inhibition of blood vessel growth (hemeangiogenesis) in the suture-induced inflammatory neovascularization mouse model utilizing the anti-VEGF protein Aflibercept Both, the diluted commercial aqueous composition ("Afli"; 5 mg/ml aflibercept dissolved in 10 mM sodium phosphate buffer, pH 6.2) as well as the non-aqueous ophthalmic suspension of protein powder preparations (comprising aflibercept) in F6H8 ("Afli/F6H8"; 5 mg/ml aflibercept suspended in F6H8) significantly inhibited the ingrowth of blood vessels ($p<0.05$).

Figure 2:
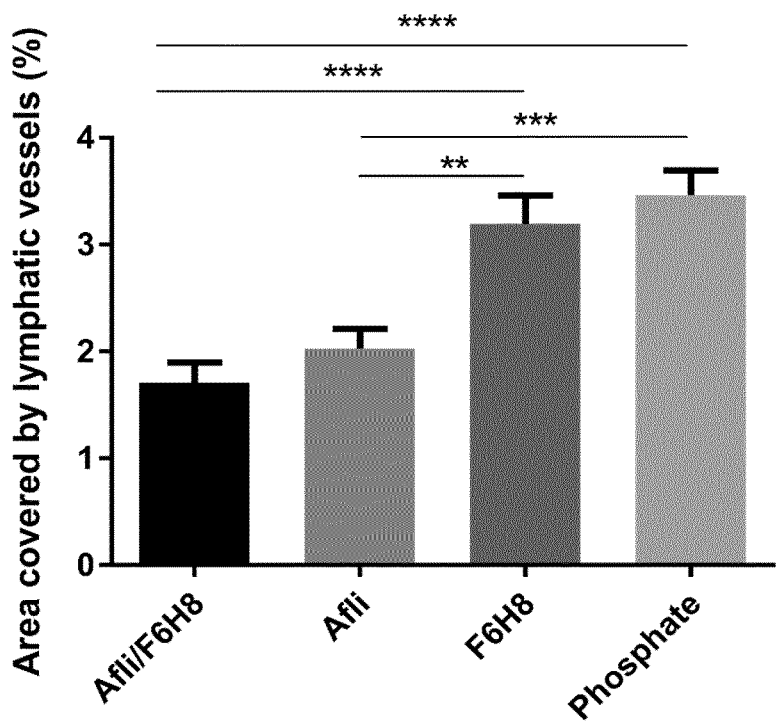
FIG. 2: Inhibition of lymph vessel growth (lymphangiogenesis) in suture-induced inflammatory neovascularization mouse model utilizing the anti-VEGF protein aflibercept. Afli/F6H8=protein powder preparation of aflibercept suspended in 1-perfluorohexyloctane (F6H8) at a protein concentration of 5 mg/ml; Afli=aflibercept aqueous solution in 10 mM sodium phosphate buffer, pH 6.2 at a protein concentration of 5 mg/ml; F6H8=vehicle (1-perfluorohexyloctane); Phosphate=control (aqueous 10 mM sodium phosphate buffer, pH 6.2).

FIG. 2 shows the inhibition of lymph vessel growth (lymphangiogenesis) in the suture-induced inflammatory neovascularization mouse model utilizing the anti-VEGF protein Aflibercept Both, the diluted commercial aqueous composition ("Afli"; 5 mg/ml aflibercept dissolved in 10 mM sodium phosphate buffer, pH 6.2) as well as the non-aqueous ophthalmic suspensions of protein powder preparations (comprising aflibercept) in F6H8 ("Afli/F6H8"; 5 mg/ml aflibercept, suspension in F6H8) significantly inhibited the ingrowth of lymph vessels ($p<0.01$).

Figure 3:
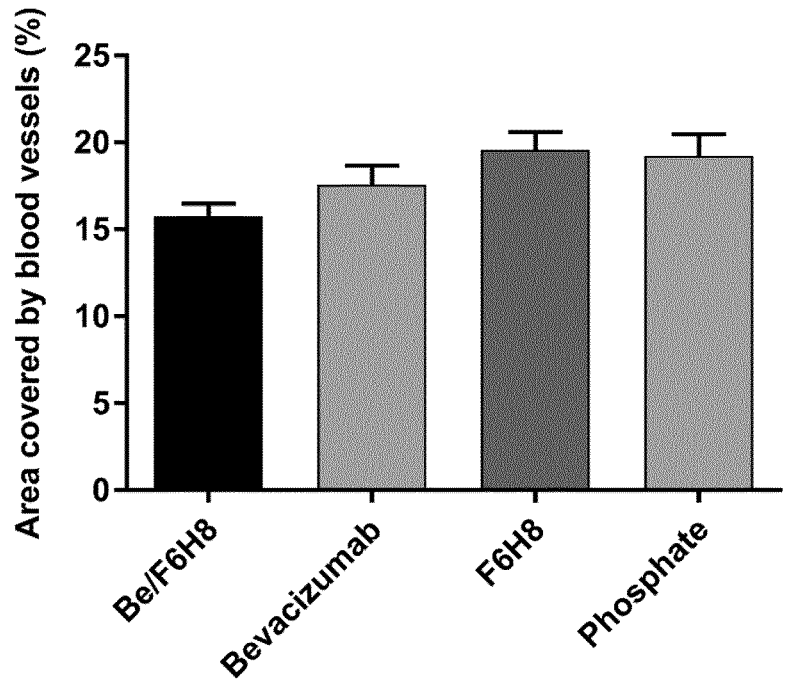
FIG. 3: Inhibition of blood vessel growth (hemeangiogenesis) in suture-induced inflammatory neovascularization mouse model utilizing the anti-VEGF protein bevacizumab. Be/F6H8=protein powder preparation of bevacizumab suspended in 1-perfluorohexyloctane (F6H8) at a protein concentration of 5 mg/ml; Bevacizumab=bevacizumab aqueous solution in 10 mM sodium phosphate buffer, pH 6.2 at a protein concentration of 5 mg/ml; F6H8=vehicle (1-perfluorohexyloctane); Phosphate=control (aqueous 10 mM sodium phosphate buffer, pH 6.2).

FIG. 3 shows the inhibition of blood vessel growth (hemeangiogenesis) in the suture-induced inflammatory neovascularization mouse model utilizing the anti-VEGF protein avastin. Both, the diluted commercial aqueous composition ("Bevacizumab"; 5 mg/ml dissolved in 10 mM sodium phosphate buffer, pH 6.2) as well as the non-aqueous ophthalmic suspension of protein powder preparations (comprising bevacizumab) in F6H8 ("Be/F6H8"; 5 mg/ml bevacizumab; suspension in F6H8) inhibited the ingrowth of blood vessels.

Figure 4:
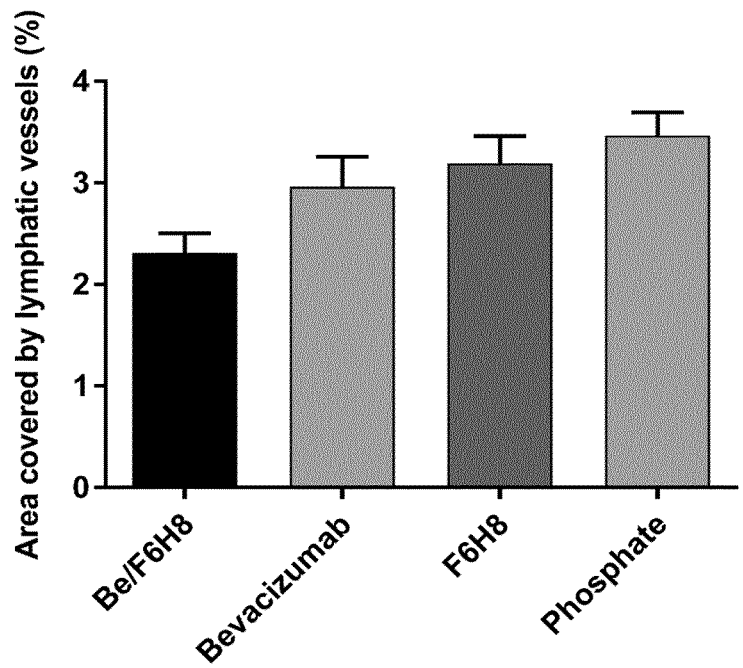
FIG. 4: Inhibition of lymph vessel growth (lymphangiogenesis) in suture-induced inflammatory neovascularization mouse model utilizing the anti-VEGF protein bevacizumab. Be/F6H8=protein powder preparation of bevacizumab suspended in 1-perfluorohexyloctane (F6H8) at a protein concentration of 5 mg/ml; Afli=bevacizumab aqueous solution in 10 mM sodium phosphate buffer, pH 6.2 at a protein concentration of 5 mg/ml; F6H8=vehicle (1-perfluorohexyloctane); Phosphate=control (aqueous 10 mM sodium phosphate buffer, pH 6.2).

FIG. 4 shows inhibition of lymph vessel growth (lymphangiogenesis) in the suture-induced inflammatory neovascularization mouse model utilizing the anti-VEGF protein avastin. Both, the diluted commercial aqueous composition ("Bevacizumab"; 5 mg/ml dissolved in 10 mM sodium phosphate buffer, pH 6.2) as well as the non-aqueous ophthalmic suspension of protein powder preparations (comprising bevacizumab) in F6H8 ("Be/F6H8"; 5 mg/ml bevacizumab; suspension in F6H8) inhibited the ingrowth of lymph vessels.

The invention claimed is:

1. A method of treatment of corneal neovascularization and/or corneal angiogenesis, comprising administering a non-aqueous topical ophthalmic composition topically to the eye or an ophthalmic tissue of a subject in need thereof, wherein the composition comprises particles of a protein powder preparation suspended in a liquid vehicle comprising a semifluorinated alkane, wherein the particles of the protein powder preparation comprise aflibercept.

2. The method according to claim 1, wherein the particles of the protein powder preparation are obtained by spray-drying or lyophilization of an aqueous composition comprising the aflibercept.

3. The method according to claim 1, wherein the particles of the protein powder preparation further comprise one or more protein stabilizing agents selected from polyols, sugars, amino acids, amines and salting out salts, polymers, surfactants, and arginine.

4. The method according to claim 1, wherein the concentration of the aflibercept in the composition is between about 1 to 60 mg/ml, or about 5 mg/ml.

5. The method according to claim 1, wherein the size of 90% of the suspended particles of the protein powder preparation is between 1 to 100 µm, as measured by laser diffraction.

6. The method according to claim 1, wherein the semifluorinated alkane is selected from F4H4, F4H5, F4H6, F6H4, F6H6, F6H8, and F8H8.

7. The method according to claim 1, wherein the method is for the treatment of ocular neovascularization.

8. The method according to claim 1, wherein the method provides inhibition of growth of blood vessels and/or lymphatic vessels.

9. The method according to claim 1, wherein the method is for the treatment of and/or corneal angiogenesis.

10. The method according to claim 1, wherein the subject is undergoing corneal transplantation.

11. The method according to claim 1, wherein the particles of the protein powder preparation further comprise one or more protein stabilizing agents selected from sugars.

12. The method according to claim 11, wherein the sugar is sucrose.

13. The method according to claim 1, wherein the semifluorinated alkane is F6H8.

14. The method according to claim 1, wherein the concentration of the aflibercept in the composition is between about 1 to 25 mg/ml, the semifluorinated alkane is F6H8, and wherein the particles of the protein powder preparation further comprise one or more protein stabilizing agents comprising sucrose.

* * * * *